United States Patent [19]

Wenderoth et al.

[11] Patent Number: 5,112,862
[45] Date of Patent: May 12, 1992

[54] 3-METHOXIMINOPROPIONIC ESTERS AND FUNGICIDES CONTAINING THEM

[75] Inventors: Bernd Wenderoth, Lampertheim; Hubert Sauter, Mannheim; Franz Roehl; Eberhard Ammermann, both of Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 546,880

[22] Filed: Jul. 2, 1990

[30] Foreign Application Priority Data

Jul. 13, 1989 [DE] Fed. Rep. of Germany ....... 3923093

[51] Int. Cl.$^5$ .................................. A01N 37/34
[52] U.S. Cl. .................................. 514/522; 514/530; 514/531; 514/539; 558/414; 560/9; 560/10; 560/21; 560/35
[58] Field of Search ............... 560/35, 9, 10, 21; 514/522, 530, 531, 539; 558/414

[56] References Cited

U.S. PATENT DOCUMENTS 4,709,078 11/1987 Schirmer et al. .
4,723,034 2/1988 Schirmer et al. .
4,782,177 11/1988 Schirmer et al. .
4,822,908 4/1989 Karbach et al. .
4,829,085 5/1989 Wenderoth et al. .

FOREIGN PATENT DOCUMENTS 254426 1/1988 European Pat. Off. .

Primary Examiner—Bruce Gray
Attorney, Agent, or Firm—Oblon, Spivak, McClelland, Maier & Neustadt

[57] ABSTRACT

3-Methoximinopropionic esters of the formula

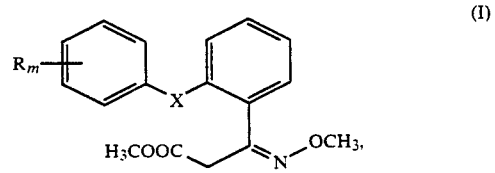

(I)

where the radicals R (m=1 to 5) are each hydrogen, halogen, cyano, nitro, alkyl, cycloalkyl, alkenyl, alkoxy, haloalkyl, haloalkoxy, unsubstituted or substituted phenyl, unsubstituted or substituted phenoxy, unsubstituted or substituted benzyl or unsubstituted or substituted benzyloxy, or the group

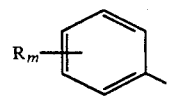

is naphthyl, and X is methyleneoxy, oxymethylene, ethylene, ethenylene, thiomethylene or oxygen, and fungicides containing these compounds.

8 Claims, No Drawings

3-METHOXIMINOPROPIONIC ESTERS AND FUNGICIDES CONTAINING THEM

The present invention relates to novel 3-methoximinopropionic esters and fungicides containing them. It is known that oxime ether derivatives, for example methyl 2-(2-methylbenzyloxy)-phenylglyoxylateO-methyloxime, can be used as fungicides (European Patent 253,213). However, their action is often inadequate for some indications.

We have found that novel 3-methoximinopropionic esters of the general formula I

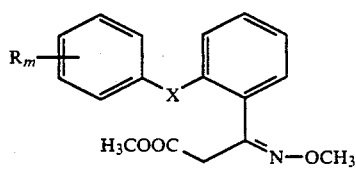

where the radicals R (m=1 to 5) are identical or different and are each hydrogen, halogen, cyano, nitro, $C_1$-$C_{15}$-alkyl, $C_3$-$C_6$-cycloalkyl, $C_3$-$C_6$-alkenyl, $C_1$-$C_4$-alkoxy, $C_1$-or $C_2$-haloalkyl, $C_1$- or $C_2$-haloalkoxy, unsubstituted or substituted phenyl, unsubstituted or substituted phenoxy, unsubstituted or substituted benzyl or unsubstituted or substituted benzyloxy, or the group

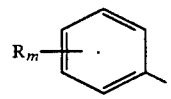

is α-naphthyl or β-naphthyl, and X is methyleneoxy, oxymethylene, ethylene, ethenylene, thiomethylene or oxygen, have an excellent fungicidal action which is better than that of the known ether derivatives.

The radicals stated in the general formula I have, for example, the following meanings: R (m=1 to 5) may be, for example: hydrogen, halogen (e.g. fluorine, chlorine, bromine or iodine), cyano, nitro, $C_1$-$C_{15}$-alkyl, (e.g. methyl, ethyl, n-propyl, isopropyl, n-butyl, isobutyl, sec-butyl, tert-butyl, pentyl, hexyl, heptyl, octyl, nonyl or decyl), $C_3$-$C_6$-cycloalkyl (e.g. cyclopropyl, cyclopentyl or cyclohexyl), $C_3$-$C_6$-alkenyl (e.g. 1-propenyl or 2-propenyl), $C_1$-$C_4$-alkoxy (e.g. methoxy, ethoxy, n-propoxy, isopropoxy, n-butoxy or tert-butoxy), $C_1$- or $C_2$-haloalkyl (e.g. difluoromethyl, trifluoromethyl, chloromethyl, dichloromethyl, trichloromethyl or pentafluoroethyl), $C_1$- or $C_2$-haloalkoxy (e.g. trifluoromethoxy, difluoromethoxy, tetrafluoroethoxy or pentafluoroethoxy), unsubstituted or substituted phenyl (e.g. phenyl, $C_1$-$C_4$-alkylphenyl or halophenyl), unsubstituted or substituted phenoxy (e.g. phenoxy, $C_1$-$C_4$-alkylphenoxy or halophenoxy), unsubstituted or substituted benzyl (e.g. benzyl or halobenzyl) or unsubstituted or substituted benzyloxy (e.g. benzyloxy, halobenzyloxy or $C_1$-$C_4$-alkylbenzyloxy). Furthermore, the group

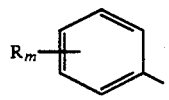

may be α-naphthyl or β-naphthyl.

X is preferably —$CH_2O$—, —$OCH_2$—, —$CH_2$—$CH_2$—, —$CH$=$CH$— or an —$SCH_2$ chain or is O.
m is 1, 2, 3, 4 or 5, preferably from 1 to 3.

Because of the C=N double bond, the novel compounds of the general formula I may occur both as E isomers and as X isomers. Both the individual isomeric compounds and mixtures thereof form subjects of the invention and can be used as fungicides.

The novel compounds of the general formula I can be prepared, for example, by the following processes.

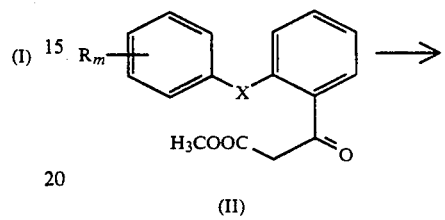

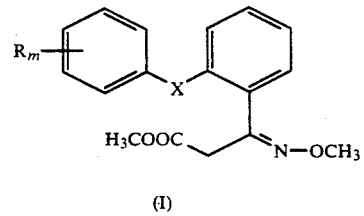

The β-ketoesters of the general formula II may be converted into the novel compounds of the general formula I by reacting them with O-methylhydroxylamine (cf. e.g. H. V. Secor and E. B. Sanders, J. Org. Chem. 43 (1978), 2539–2541) or by reacting them first with hydroxylamine to give the corresponding oxime and then reacting the latter with a methylating agent, e.g. methyl iodide or dimethyl sulfate (cf. also European Patent 253,213).

The β-ketoesters of the general structure II are novel and useful intermediates and likewise form the subject of this invention.

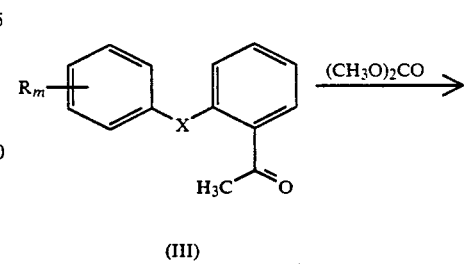

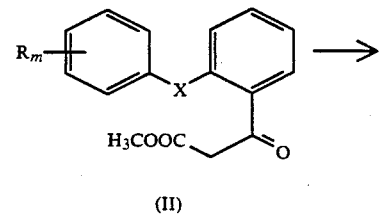

They can be prepared by conventional processes (cf. F. W. Swamer and Ch. R. Hauser, J. Am. Chem. Soc. 72 (1950), 1352–1356), by reacting an acetophenone of the general formula III, in a suitable solvent, e.g. diethyl ether, with dimethyl carbonate in the presence of a suitable base, e.g. sodium hydride or sodium methoxide.

Acetophenone derivatives of the general formula IIIa (X=CH₂O) can be prepared in a conventional manner by reacting a benzyl halide of the general formula IV, where Hal is halogen and R$_m$ has the abovementioned meanings, with 2-hydroxyacetophenone in the presence of a base, e.g. sodium carbonate, and of a suitable solvent, e.g. methanol.

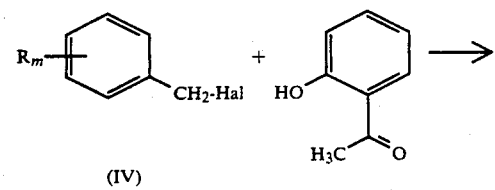

(IV)

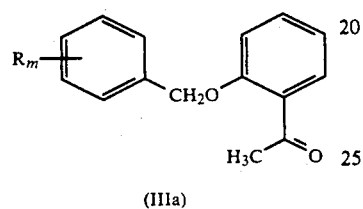

(IIIa)

Acetophenone derivatives of the general formula IIIb (X=OCH₂) can be prepared in a conventional manner by reacting a phenol of the general formula V, where R$_m$ has the abovementioned meanings, with 2-cyanobenzyl bromide in the presence of a base, e.g. sodium carbonate, and of a suitable solvent, e.g. methanol.

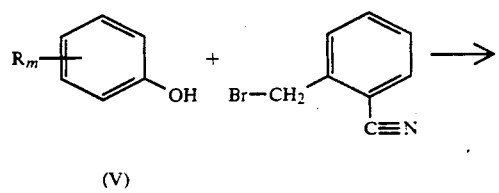

(V)

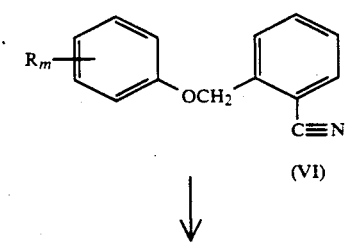

(VI)

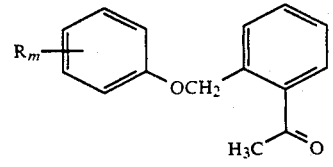

(IIIb)

The resulting nitrile of the general formula VI can be converted into the acetophenone IIIb by a Grignard reaction with a methylmagnesium halide (cf. E. C. Ashby et al., J. Am. Chem. Soc. 95 (1973), 4896, 5186).

If the analogous thiophenols of the general formula VII are used as starting materials, the acetophenone derivatives of the general formula IIIc (X=SCH₂) are obtained by the same route

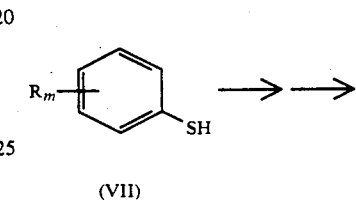

(VII)

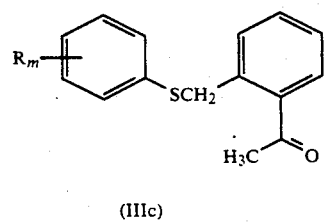

(IIIc)

Acetophenone derivatives of the general formula IIId (X=CH=CH) can be prepared in a known manner by subjecting 2-cyanobenzaldehyde to a Wittig reaction (cf. G. Wittig and U. Schöllkopf, Org. Synth. Coll. Vol. V, 751 (1973)) with a benzylphosphonium halide of the general formula VIII, where R$_m$ has the abovementioned meanings.

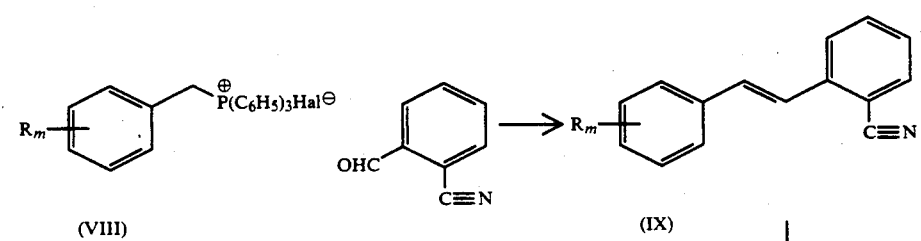

(VIII)          (IX)

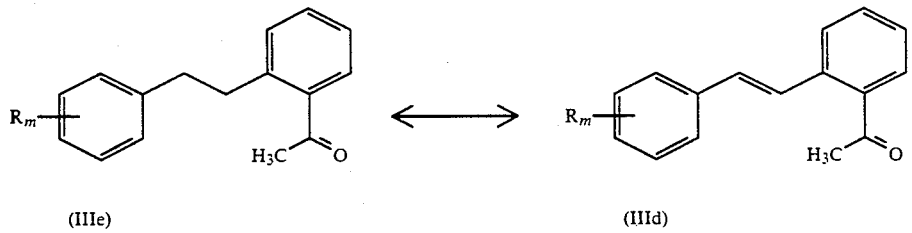

The resulting nitrile of the general formula IX can be converted into the acetophenone IIId by a Grignard reaction with a methylmagnesium halide (cf. E. C. Ashby et al., J. Am. Chem. Soc. 95 (1973), 4896, 5186).

By reducing the double bond either catalytically with hydrogen (cf. Houben-Weyl, Methoden der organischen Chemie V/2b, 264–267 (1981)) or with diimine (cf. E. E. van Tamelen et al., J. Am. Chem. Soc. 83 (1961), 4302), the acetophenone derivatives of the general formula IIIe ($X=CH_2-CH_2$) can be prepared therefrom.

Acetophenone derivatives of the general formula IIIf ($X=O$) can be prepared, for example, in a known manner (T. W. Harris et al., J. Med. Chem. 25 (1982), 855–858), by reacting 2-chloroacetophenone with a phenol of the formula V in the presence of copper powder and potassium carbonate.

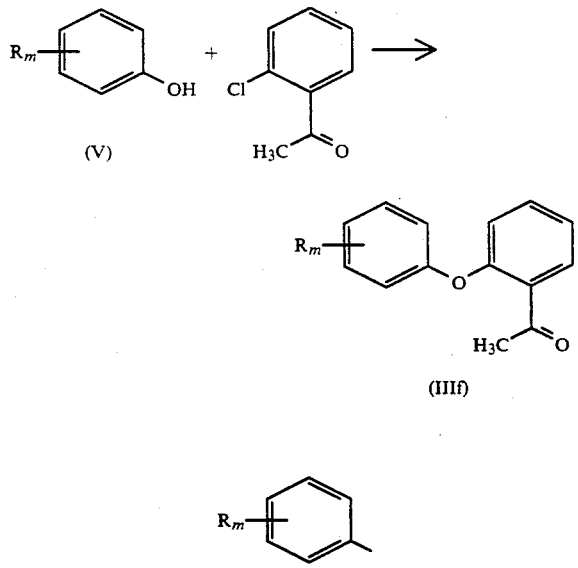

The Examples which follow illustrate the preparation of the novel compounds according to the invention:

METHOD 1

2-(2-Methylbenzyloxy)-acetophenone 102 g (0.75 mol) of 2-hydroxyacetophenone and 102 g (0.75 mol) of potassium carbonate in 500 ml of absolute ethanol are initially taken. 139 g (0.75 mol) of 2-methylbenzyl bromide are added dropwise and the mixture is refluxed for 10 h. The mixture is cooled and filtered under suction, after which the filtrate is evaporated down. The crude product is recrystallized from diethyl ether. 106 g (59%) of product are obtained as crystals (mp.=53°–55° C.).

METHOD 2

Methyl 3-[2-(2-methylbenzyloxy)-phenyl]-3-oxopropionate 14 g (0.6 mol) of 100% pure sodium hydride and 54 g (0.6 mol) of dimethyl carbonate in 225 ml of absolute diethyl ether are initially taken under nitrogen. 72 g (0.3 mol) of 2-(2-methylbenzyloxy)-acetophenone, dissolved in 300 ml of absolute ether, are added dropwise at 20°–35° C. and the mixture is refluxed for 5 h. At 10° C., first 45 ml of methanol and then 100 ml of $H_2O$ are slowly added dropwise. The pH is then brought to 7 with dilute hydrochloric acid. The organic phase is washed several times with $H_2O$, dried over sodium sulfate and evaporated down. The product is obtained in quantitative yield as crystals (mp.=38°–42° C.).

$^1$H-NMR: δ=2.39 (s, 3H); 3.55 (s, 2H); 5.15 (s, 2H), 7.0–7.9 (m, 8H).

PREPARATION EXAMPLE 1

Methyl 3-[2-(2-methylbenzyloxy)-phenyl]-3-methoximinopropionate (compound No. 66)

14.9 g (0.05 mol) of methyl 3-[2-(2-methylbenzyloxy)-phenyl]-3-oxopropionate and 8.35 g (0.1 mol) of O-methylhydroxylamine hydrochloride in 250 ml of pyridine are initially taken and then stirred for 18 h at 70° C. The mixture is then evaporated down under reduced pressure. The residue is taken up in ethyl acetate and the solution is washed thoroughly with $H_2O$, dried over sodium sulfate and evaporated down again. 12 g (73%) of the desired ester are obtained as an oil (isomer ratio 85:15).

$^1$H-NMR (CDCl$_3$): δ=2.35 (m, 3H); 3.30/3.59 (2×s, 3H); 3.56/3.75 (2×s, 2H); 3.85/3.96 (2×s, 3H); 5.05 (s, 2H); 6.9–7.5 (m, 8H).

The following compounds can be prepared in a similar manner.

TABLE 1

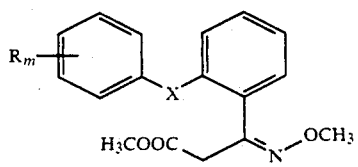

| No. | $R_m$ | X | mp (°C.) | IR(cm$^{-1}$) |
|---|---|---|---|---|
| 1 | H | CH$_2$O | | |
| 2 | 2-F | CH$_2$O | | |
| 3 | 3-F | CH$_2$O | | |
| 4 | 4-F | CH$_2$O | oil | 2940,1741,1512,1226,1050,754 |
| 5 | 2,3-F$_2$ | CH$_2$O | | |
| 6 | 2,4-F$_2$ | CH$_2$O | | |
| 7 | 2,4,6-F$_3$ | CH$_2$O | | |
| 8 | 2,3,4,5,6-F$_5$ | CH$_2$O | | |
| 9 | 2-Cl | CH$_2$O | | |
| 10 | 3-Cl | CH$_2$O | | |
| 11 | 4-Cl | CH$_2$O | oil | 2940,1741,1494,1234,1050,754 |
| 12 | 2,3-Cl$_2$ | CH$_2$O | | |
| 13 | 2,4-Cl$_2$ | CH$_2$O | | |
| 14 | 2,5-Cl$_2$ | CH$_2$O | | |
| 15 | 2,6-Cl$_2$ | CH$_2$O | | |
| 16 | 3,4-Cl$_2$ | CH$_2$O | | |
| 17 | 3,5-Cl$_2$ | CH$_2$O | | |
| 18 | 2,3,4-Cl$_3$ | CH$_2$O | | |
| 19 | 2,3,5-Cl$_3$ | CH$_2$O | | |
| 20 | 2,3,6-Cl$_3$ | CH$_2$O | | |
| 21 | 2,4,5-Cl$_3$ | CH$_2$O | | |
| 22 | 2,4,6-Cl$_3$ | CH$_2$O | | |
| 23 | 3,4,5-Cl$_3$ | CH$_2$O | | |
| 24 | 2,3,4,6-Cl$_4$ | CH$_2$O | | |
| 25 | 2,3,5,6-Cl$_4$ | CH$_2$O | | |
| 26 | 2,3,4,5,6-Cl$_5$ | CH$_2$O | | |
| 27 | 2-Br | CH$_2$O | | |
| 28 | 3-Br | CH$_2$O | | |
| 29 | 4-Br | CH$_2$O | 91–95 | 2940,1746,1447,1176,1044,751 |
| 30 | 2,4-Br$_2$ | CH$_2$O | | |
| 31 | 2,5-Br$_2$ | CH$_2$O | | |
| 32 | 2,6-Br$_2$ | CH$_2$O | | |
| 33 | 2,4,6-Br$_3$ | CH$_2$O | | |
| 34 | 2,3,4,5,6-Br$_5$ | CH$_2$O | | |
| 35 | 2-I | CH$_2$O | | |
| 36 | 2-I | CH$_2$O | | |
| 37 | 4-I | CH$_2$O | | |
| 38 | 2,4-I$_2$ | CH$_2$O | | |
| 39 | 2-Cl, 4-F | CH$_2$O | | |
| 40 | 2-Cl, 4-F | CH$_2$O | | |
| 41 | 2-Cl, 5-F | CH$_2$O | | |
| 42 | 2-Cl, 6-F | CH$_2$O | | |
| 43 | 2-Cl, 3-Br | CH$_2$O | | |
| 44 | 2-Cl, 4-Br | CH$_2$O | | |
| 45 | 2-Cl, 5-Br | CH$_2$O | | |
| 46 | 2-Cl, 6-Br | CH$_2$O | | |
| 47 | 2-Br, 3-Cl | CH$_2$O | | |
| 48 | 2-Br, 4-Cl | CH$_2$O | | |
| 49 | 2-Br, 5-Cl | CH$_2$O | | |
| 50 | 2-Br, 3-F | CH$_2$O | | |
| 51 | 2-Br, 4-F | CH$_2$O | | |
| 52 | 2-Br, 5-F | CH$_2$O | | |
| 53 | 2-Br, 6-F | CH$_2$O | | |
| 54 | 2-F, 3-Cl | CH$_2$O | | |
| 55 | 2-F, 4-Cl | CH$_2$O | | |
| 56 | 2-F, 5-Cl | CH$_2$O | | |
| 57 | 3-Cl, 4-F | CH$_2$O | | |
| 58 | 3-Cl, 5-F | CH$_2$O | | |
| 59 | 3-Cl, 4-Br | CH$_2$O | | |
| 60 | 3-Cl, 5-Br | CH$_2$O | | |
| 61 | 3-F, 4-Cl | CH$_2$O | | |
| 62 | 3-F, 4-Br | CH$_2$O | | |
| 63 | 3-Br, 4-Cl | CH$_2$O | | |
| 64 | 3-Br, 4-F | CH$_2$O | | |
| 65 | 2,6-Cl$_2$, 4-Br | CH$_2$O | | |
| 66 | 2-CH$_3$ | CH$_2$O | oil | 2940,1742,1450,1231,1050,751 |
| 67 | 3-CH$_3$ | CH$_2$O | | |
| 68 | 4-CH$_3$ | CH$_2$O | | |
| 69 | 2,3-(CH$_3$)$_2$ | CH$_2$O | | |
| 70 | 2,4-(CH$_3$)$_2$ | CH$_2$O | | |
| 71 | 2,5-(CH$_3$)$_2$ | CH$_2$O | | |
| 72 | 2,6-(CH$_3$)$_2$ | CH$_2$O | | |

TABLE 1-continued

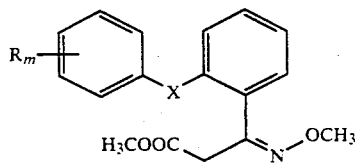

(I)

| No. | $R_m$ | X | mp (°C.) | IR(cm$^{-1}$) |
|---|---|---|---|---|
| 73 | 3,4-(CH$_3$)$_2$ | CH$_2$O | | |
| 74 | 3,5-(CH$_3$)$_2$ | CH$_2$O | | |
| 75 | 2,3,4-(CH$_3$)$_3$ | CH$_2$O | | |
| 76 | 2,3,5-(CH$_3$)$_3$ | CH$_2$O | | |
| 77 | 2,3,6-(CH$_3$)$_3$ | CH$_2$O | | |
| 78 | 2,4,5-(CH$_3$)$_3$ | CH$_2$O | | |
| 79 | 2,4,6-(CH$_3$)$_3$ | CH$_2$O | | |
| 80 | 3,4,5-(CH$_3$)$_3$ | CH$_2$O | | |
| 81 | 2,3,4,6-(CH$_3$)$_4$ | CH$_2$O | | |
| 82 | 2,3,5,6-(CH$_3$)$_4$ | CH$_2$O | | |
| 83 | 2,3,4,5,6-(CH$_3$)$_5$ | CH$_2$O | | |
| 84 | 2-C$_2$H$_5$ | CH$_2$O | | |
| 85 | 3-C$_2$H$_5$ | CH$_2$O | | |
| 86 | 4-C$_2$H$_5$ | CH$_2$O | | |
| 87 | 2,4-(C$_2$H$_5$)$_2$ | CH$_2$O | | |
| 88 | 2,6-(C$_2$H$_5$)$_2$ | CH$_2$O | | |
| 89 | 3,5-(C$_2$H$_5$)$_2$ | CH$_2$O | | |
| 90 | 2,4,6-(C$_2$H$_5$)$_3$ | CH$_2$O | | |
| 91 | 2-n-C$_3$H$_7$ | CH$_2$O | | |
| 92 | 3-n-C$_3$H$_7$ | CH$_2$O | | |
| 93 | 4-n-C$_3$H$_7$ | CH$_2$O | | |
| 94 | 2-i-C$_3$H$_7$ | CH$_2$O | | |
| 95 | 3-i-C$_3$H$_7$ | CH$_2$O | | |
| 96 | 4-i-C$_3$H$_7$ | CH$_2$O | | |
| 97 | 2,4-(i-C$_3$H$_7$)$_2$ | CH$_2$O | | |
| 98 | 2,6-(i-C$_3$H$_7$)$_2$ | CH$_2$O | | |
| 99 | 3,5-(i-C$_3$H$_7$)$_2$ | CH$_2$O | | |
| 100 | 2,4,6-(i-C$_3$H$_7$)$_3$ | CH$_2$O | | |
| 101 | 2-s-C$_4$H$_9$ | CH$_2$O | | |
| 102 | 3-s-C$_4$H$_9$ | CH$_2$O | | |
| 103 | 4-s-C$_4$H$_9$ | CH$_2$O | | |
| 104 | 2-t-C$_4$H$_9$ | CH$_2$O | | |
| 105 | 3-t-C$_4$H$_9$ | CH$_2$O | | |
| 106 | 4-t-C$_4$H$_9$ | CH$_2$O | | |
| 107 | 2,3-(t-C$_4$H$_9$)$_2$ | CH$_2$O | | |
| 108 | 2,4-(t-C$_4$H$_9$)$_2$ | CH$_2$O | | |
| 109 | 2,5-(t-C$_4$H$_9$)$_2$ | CH$_2$O | | |
| 110 | 2,6-(t-C$_4$H$_9$)$_2$ | CH$_2$O | | |
| 111 | 3,5-(t-C$_4$H$_9$)$_2$ | CH$_2$O | | |
| 112 | 2,4,6-(t-C$_4$H$_9$)$_3$ | CH$_2$O | | |
| 113 | 4-n-C$_9$H$_{19}$ | CH$_2$O | | |
| 114 | 4-n-C$_{12}$H$_{25}$ | CH$_2$O | | |
| 115 | 3-n-C$_{15}$H$_{31}$ | CH$_2$O | | |
| 116 | 4-(1,1,3,3,-tetramethylbutyl) | CH$_2$O | | |
| 117 | 4-(1,1,3,-trimethylbutyl) | CH$_2$O | | |
| 118 | 2-t-C$_4$H$_9$, 4-CH$_3$ | CH$_2$O | | |
| 119 | 2-t-C$_4$H$_9$, 5-CH$_3$ | CH$_2$O | | |
| 120 | 2,6-(t-C$_4$H$_9$)$_2$, 4-CH$_3$ | CH$_2$O | | |
| 121 | 2-CH$_3$, 4-t-C$_4$H$_9$ | CH$_2$O | | |
| 122 | 2-CH$_3$, 6-t-C$_4$H$_9$ | CH$_2$O | | |
| 123 | 2-CH$_3$, 4-i-C$_3$H$_7$ | CH$_2$O | | |
| 124 | 2-CH$_3$, 5-i-C$_3$H$_7$ | CH$_2$O | | |
| 125 | 3-CH$_3$, 4-i-C$_3$H$_7$ | CH$_2$O | | |
| 126 | 2-i-C$_3$H$_7$, 5-CH$_3$ | CH$_2$O | | |
| 127 | 2,4-(t-C$_4$H$_9$)$_2$, 6-i-C$_3$H$_7$ | CH$_2$O | | |
| 128 | 2-C$_3$H$_5$ (= allyl) | CH$_2$O | | |
| 129 | 3-C$_3$H$_5$ | CH$_2$O | | |
| 130 | 4-C$_3$H$_5$ | CH$_2$O | | |
| 131 | 2-C$_3$H$_5$, 6-CH$_3$ | CH$_2$O | | |
| 132 | 2-cyclo-C$_6$H$_{11}$ | CH$_2$O | | |
| 133 | 3-cyclo-C$_6$H$_{11}$ | CH$_2$O | | |
| 134 | 4-cyclo-C$_6$H$_{11}$ | CH$_2$O | | |
| 135 | 2,4-(cyclo-C$_6$H$_{11}$)$_2$, 6-CH$_3$ | CH$_2$O | | |
| 136 | 2-CH$_3$, 4-cyclo-C$_6$H$_{11}$ | CH$_2$O | | |
| 137 | 2-CH$_3$, 4-(1,1,3,3-tetramethylbutyl) | CH$_2$O | | |
| 138 | 2-CH$_2$C$_6$H$_5$ | CH$_2$O | | |
| 139 | 3-CH$_2$C$_6$H$_5$ | CH$_2$O | | |
| 140 | 4-CH$_2$C$_6$H$_5$ | CH$_2$O | | |
| 141 | 2-CH$_2$C$_6$H$_5$, 4-CH$_3$ | CH$_2$O | | |
| 142 | 2-CH$_3$, 4-CH$_2$C$_6$H$_5$ | CH$_2$O | | |
| 143 | 2-C$_6$H$_5$ | CH$_2$O | | |
| 144 | 3-C$_6$H$_5$ | CH$_2$O | | |

TABLE 1-continued

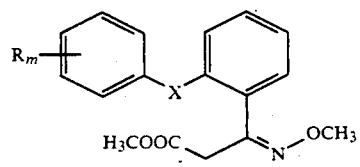
(I)

| No. | $R_m$ | X | mp (°C.) | IR(cm$^{-1}$) |
|---|---|---|---|---|
| 145 | 4-C$_6$H$_5$ | CH$_2$O | | |
| 146 | 4-(2-i-C$_3$H$_7$—C$_6$H$_4$) | CH$_2$O | | |
| 147 | 4-C$_6$H$_5$, 2,6-(CH$_3$)$_2$ | CH$_2$O | | |
| 148 | 2-Cl, 4-C$_6$H$_5$ | CH$_2$O | | |
| 149 | 2-Br, 4-C$_6$H$_5$ | CH$_2$O | | |
| 150 | 2-C$_6$H$_5$, 4-Cl | CH$_2$O | | |
| 151 | 2-C$_6$H$_5$, 4-Br | CH$_2$O | | |
| 152 | 2-CH$_2$C$_6$H$_5$, 4-Cl | CH$_2$O | | |
| 153 | 2-CH$_2$C$_6$H$_5$, 4-Br | CH$_2$O | | |
| 154 | 2-Cl, 4-CH$_2$C$_6$H$_5$ | CH$_2$O | | |
| 155 | 2-Br, 4-CH$_2$C$_6$H$_5$ | CH$_2$O | | |
| 156 | 2-cyclo-C$_6$H$_{11}$, 4-Cl | CH$_2$O | | |
| 157 | 2-cyclo-C$_6$H$_{11}$, 4-Br | CH$_2$O | | |
| 158 | 2-Cl, 4-cyclo-C$_6$H$_{11}$ | CH$_2$O | | |
| 159 | 2-Br, 4-cyclo-C$_6$H$_{11}$ | CH$_2$O | | |
| 160 | 2-OCH$_3$ | CH$_2$O | | |
| 161 | 3-OCH$_3$ | CH$_2$O | | |
| 162 | 4-OCH$_3$ | CH$_2$O | | |
| 163 | 2,4-(OCH$_3$)$_2$ | CH$_2$O | | |
| 164 | 2-OC$_2$H$_5$ | CH$_2$O | | |
| 165 | 3-OC$_2$H$_5$ | CH$_2$O | | |
| 166 | 4-OC$_2$H$_5$ | CH$_2$O | | |
| 167 | 2-OCH$_2$C$_6$H$_5$ | CH$_2$O | | |
| 168 | 3-OCH$_2$C$_6$H$_5$ | CH$_2$O | | |
| 169 | 4-OCH$_2$C$_6$H$_5$ | CH$_2$O | | |
| 170 | 2-O-t-C$_4$H$_9$ | CH$_2$O | | |
| 171 | 3-O-t-C$_4$H$_9$ | CH$_2$O | | |
| 172 | 4-O-t-C$_4$H$_9$ | CH$_2$O | | |
| 173 | 2-OC$_6$H$_5$ | CH$_2$O | | |
| 174 | 3-OC$_6$H$_5$ | CH$_2$O | | |
| 175 | 4-OC$_6$H$_5$ | CH$_2$O | | |
| 176 | 2-CF$_3$ | CH$_2$O | | |
| 177 | 3-CF$_3$ | CH$_2$O | | |
| 178 | 4-CF$_3$ | CH$_2$O | | |
| 179 | 2-OCF$_3$ | CH$_2$O | | |
| 180 | 3-OCF$_3$ | CH$_2$O | | |
| 181 | 4-OCF$_3$ | CH$_2$O | | |
| 182 | 3-OCH$_2$CHF$_2$ | CH$_2$O | | |
| 183 | 3-OCF$_2$CHF$_2$ | CH$_2$O | | |
| 184 | 3-OC$_2$H$_5$ | CH$_2$O | | |
| 185 | 2-NO$_2$ | CH$_2$O | | |
| 186 | 3-NO$_2$ | CH$_2$O | | |
| 187 | 4-NO$_2$ | CH$_2$O | | |
| 188 | 2-CN | CH$_2$O | | |
| 189 | 3-CN | CH$_2$O | | |
| 190 | 4-CN | CH$_2$O | | |
| 191 | 2-CH$_3$, 3-Cl | CH$_2$O | | |
| 192 | 2-CH$_3$, 4-Cl | CH$_2$O | | |
| 193 | 2-CH$_3$, 5-Cl | CH$_2$O | | |
| 194 | 2-CH$_3$, 6-Cl | CH$_2$O | | |
| 195 | 2-CH$_3$, 3-F | CH$_2$O | | |
| 196 | 2-CH$_3$, 4-F | CH$_2$O | | |
| 197 | 2-CH$_3$, 5-F | CH$_2$O | | |
| 198 | 2-CH$_3$, 6-F | CH$_2$O | | |
| 199 | 2-CH$_3$, 3-Br | CH$_2$O | | |
| 200 | 2-CH$_3$, 4-Br | CH$_2$O | | |
| 201 | 2-CH$_3$, 5-Br | CH$_2$O | | |
| 202 | 2-CH$_3$, 6-Br | CH$_2$O | | |
| 203 | 2-Cl, 3-CH$_3$ | CH$_2$O | | |
| 204 | 2-Cl, 4-CH$_3$ | CH$_2$O | | |
| 205 | 2-Cl, 5-CH$_3$ | CH$_2$O | | |
| 206 | 2-F, 3-CH$_3$ | CH$_2$O | | |
| 207 | 2-F, 4-CH$_3$ | CH$_2$O | | |
| 208 | 2-F, 5-CH$_3$ | CH$_2$O | | |
| 209 | 2-Br, 3-CH$_3$ | CH$_2$O | | |
| 210 | 2-Br, 4-CH$_3$ | CH$_2$O | | |
| 211 | 2-Br, 5-CH$_3$ | CH$_2$O | | |
| 212 | 3-CH$_3$, 4-Cl | CH$_2$O | | |
| 213 | 3-CH$_3$, 5-Cl | CH$_2$O | | |
| 214 | 3-CH$_3$, 4-F | CH$_2$O | | |
| 215 | 3-CH$_3$, 5-F | CH$_2$O | | |
| 216 | 3-CH$_3$, 4-Br | CH$_2$O | | |

TABLE 1-continued

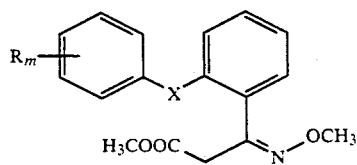

(I)

| No. | $R_m$ | X | mp (°C.) | IR(cm$^{-1}$) |
|---|---|---|---|---|
| 217 | 3-CH$_3$, 5-Br | CH$_2$O | | |
| 218 | 3-F, 4-CH$_3$ | CH$_2$O | | |
| 219 | 3-Cl, 4-CH$_3$ | CH$_2$O | | |
| 220 | 3-Br, 4-CH$_3$ | CH$_2$O | | |
| 221 | 2-Cl, 4,5-(CH$_3$)$_2$ | CH$_2$O | | |
| 222 | 2-Br, 4,5-(CH$_3$)$_2$ | CH$_2$O | | |
| 223 | 2-Cl, 3,5-(CH$_3$)$_2$ | CH$_2$O | | |
| 224 | 2-Br, 3,5-(CH$_3$)$_2$ | CH$_2$O | | |
| 225 | 2,6-Cl$_2$, 4-CH$_3$ | CH$_2$O | | |
| 226 | 2,6-F$_2$, 4-CH$_3$ | CH$_2$O | | |
| 227 | 2,6-Br$_2$, 4-CH$_3$ | CH$_2$O | | |
| 228 | 2,4-Cl$_2$, 6-CH$_3$ | CH$_2$O | | |
| 229 | 2,4-F$_2$, 6-CH$_3$ | CH$_2$O | | |
| 230 | 2,4-Br$_2$, 6-CH$_3$ | CH$_2$O | | |
| 231 | 2,6-(CH$_3$)$_2$, 4-F | CH$_2$O | | |
| 232 | 2,6-(CH$_3$)$_2$, 4-Cl | CH$_2$O | | |
| 233 | 2,6-(CH$_3$)$_2$, 4-Br | CH$_2$O | | |
| 234 | 3,5-(CH$_3$)$_2$, 4-F | CH$_2$O | | |
| 235 | 3,5-(CH$_3$)$_2$, 4-Cl | CH$_2$O | | |
| 236 | 3,5-(CH$_3$)$_2$, 4-Br | CH$_2$O | | |
| 237 | 2,3,6-(CH$_3$)$_3$, 4-F | CH$_2$O | | |
| 238 | 2,3,6-(CH$_3$)$_3$, 4-Cl | CH$_2$O | | |
| 239 | 2,3,6-(CH$_3$)$_3$, 4-Br | CH$_2$O | | |
| 240 | 2,4-(CH$_3$)$_2$, 6-F | CH$_2$O | | |
| 241 | 2,4-(CH$_3$)$_2$, 6-Cl | CH$_2$O | | |
| 242 | 2,4-(CH$_3$)$_2$, 6-Br | CH$_2$O | | |
| 243 | 2-i-C$_3$H$_7$, 4-Cl, 5-CH$_3$ | CH$_2$O | | |
| 244 | 2-CH$_3$, 4-Cl, 5-i-C$_3$H$_7$ | CH$_2$O | | |
| 245 | 2-Cl, 3-i-C$_3$H$_7$ | CH$_2$O | | |
| 246 | 2-Cl, 4-i-C$_3$H$_7$ | CH$_2$O | | |
| 247 | 2-Cl, 4-NO$_2$ | CH$_2$O | | |
| 248 | 2-NO$_2$, 4-Cl | CH$_2$O | | |
| 249 | 2-OCH$_3$, 5-NO$_2$ | CH$_2$O | | |
| 250 | 2,4-Cl$_2$, 5-NO$_2$ | CH$_2$O | | |
| 251 | 2,4-Cl$_2$, 6-NO$_2$ | CH$_2$O | | |
| 252 | 2,6-Cl$_2$, 4-NO$_2$ | CH$_2$O | | |
| 253 | 2,6-Br$_2$, 4-NO$_2$ | CH$_2$O | | |
| 254 | 2,6-I$_2$, 4-NO$_2$ | CH$_2$O | | |
| 255 | H | OCH$_2$ | | |
| 256 | 2-F | OCH$_2$ | | |
| 257 | 3-F | OCH$_2$ | | |
| 258 | 4-F | OCH$_2$ | | |
| 259 | 2,3-F$_2$ | OCH$_2$ | | |
| 260 | 2,4-F$_2$ | OCH$_2$ | | |
| 261 | 2,4,6-F$_3$ | OCH$_2$ | | |
| 262 | 2,3,4,5,6-F$_5$ | OCH$_2$ | | |
| 263 | 2-Cl | OCH$_2$ | | |
| 264 | 3-Cl | OCH$_2$ | | |
| 265 | 4-Cl | OCH$_2$ | | |
| 266 | 2,3-Cl$_2$ | OCH$_2$ | | |
| 267 | 2,4-Cl$_2$ | OCH$_2$ | | |
| 268 | 2,5-Cl$_2$ | OCH$_2$ | | |
| 269 | 2,6-Cl$_2$ | OCH$_2$ | | |
| 270 | 3,4-Cl$_2$ | OCH$_2$ | | |
| 271 | 3,5-Cl$_2$ | OCH$_2$ | | |
| 272 | 2,3,4-Cl$_3$ | OCH$_2$ | | |
| 273 | 2,3,5-Cl$_3$ | OCH$_2$ | | |
| 274 | 2,3,6-Cl$_3$ | OCH$_2$ | | |
| 275 | 2,4,5-Cl$_3$ | OCH$_2$ | | |
| 276 | 2,4,6-Cl$_3$ | OCH$_2$ | | |
| 277 | 3,4,5-Cl$_3$ | OCH$_2$ | | |
| 278 | 2,3,4,6-Cl$_4$ | OCH$_2$ | | |
| 279 | 2,3,5,6-Cl$_4$ | OCH$_2$ | | |
| 280 | 2,3,4,5,6-Cl$_5$ | OCH$_2$ | | |
| 281 | 2-Br | OCH$_2$ | | |
| 282 | 3-Br | OCH$_2$ | | |
| 283 | 4-Br | OCH$_2$ | | |
| 284 | 2,4-Br$_2$ | OCH$_2$ | | |
| 285 | 2,5-Br$_2$ | OCH$_2$ | | |
| 286 | 2,6-Br$_2$ | OCH$_2$ | | |
| 287 | 2,4,6-Br$_3$ | OCH$_2$ | | |
| 288 | 2,3,4,5,6-Br$_5$ | OCH$_2$ | | |

TABLE 1-continued

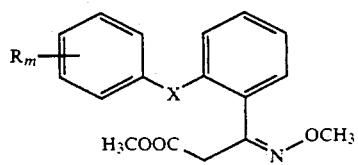

(I)

| No. | $R_m$ | X | mp (°C.) | IR(cm$^{-1}$) |
|---|---|---|---|---|
| 289 | 2-I | OCH$_2$ | | |
| 290 | 3-I | OCH$_2$ | | |
| 291 | 4-I | OCH$_2$ | | |
| 292 | 2,4-I$_2$ | OCH$_2$ | | |
| 293 | 2-Cl, 3-F | OCH$_2$ | | |
| 294 | 2-Cl, 4-F | OCH$_2$ | | |
| 295 | 2-Cl, 5-F | OCH$_2$ | | |
| 296 | 2-Cl, 3-F | OCH$_2$ | | |
| 297 | 2-Cl, 3-Br | OCH$_2$ | | |
| 298 | 2-Cl, 4-Br | OCH$_2$ | | |
| 299 | 2-Cl, 5-Br | OCH$_2$ | | |
| 300 | 2-Cl, 6-Br | OCH$_2$ | | |
| 301 | 2-Br, 3-Cl | OCH$_2$ | | |
| 302 | 2-Br, 4-Cl | OCH$_2$ | | |
| 303 | 2-Br, 5-Cl | OCH$_2$ | | |
| 304 | 2-Br, 3-F | OCH$_2$ | | |
| 305 | 2-Br, 4-F | OCH$_2$ | | |
| 305 | 2-Br, 5-F | OCH$_2$ | | |
| 307 | 2-Br, 6-F | OCH$_2$ | | |
| 308 | 2-F, 3-Cl | OCH$_2$ | | |
| 309 | 2-F, 4-Cl | OCH$_2$ | | |
| 310 | 2-F, 5-Cl | OCH$_2$ | | |
| 311 | 3-Cl, 4-F | OCH$_2$ | | |
| 312 | 3-Cl, 5-F | OCH$_2$ | | |
| 313 | 3-Cl, 4-Br | OCH$_2$ | | |
| 314 | 3-Cl, 5-Br | OCH$_2$ | | |
| 315 | 3-F, 4-Cl | OCH$_2$ | | |
| 316 | 3-F, 4-Br | OCH$_2$ | | |
| 317 | 3-Br, 4-Cl | OCH$_2$ | | |
| 318 | 3-Br, 4-F | OCH$_2$ | | |
| 319 | 2,6-Cl$_2$ | OCH$_2$ | | |
| 320 | 2-CH$_3$ | OCH$_2$ | | |
| 321 | 3-CH$_3$ | OCH$_2$ | | |
| 322 | 4-CH$_3$ | OCH$_2$ | | |
| 323 | 2,3-(CH$_3$)$_2$ | OCH$_2$ | | |
| 324 | 2,4-(CH$_3$)$_2$ | OCH$_2$ | | |
| 325 | 2,5-(CH$_3$)$_2$ | OCH$_2$ | | |
| 326 | 2,6-(CH$_3$)$_2$ | OCH$_2$ | | |
| 327 | 3,4-(CH$_3$)$_2$ | OCH$_2$ | | |
| 328 | 3,5-(CH$_3$)$_2$ | OCH$_2$ | | |
| 329 | 2,3,4-(CH$_3$)$_3$ | OCH$_2$ | | |
| 330 | 2,3,5-(CH$_3$)$_3$ | OCH$_2$ | | |
| 331 | 2,3,6-(CH$_3$)$_3$ | OCH$_2$ | | |
| 332 | 2,4,5-(CH$_3$)$_3$ | OCH$_2$ | | |
| 333 | 2,4,6-(CH$_3$)$_3$ | OCH$_2$ | | |
| 334 | 3,4,5-(CH$_3$)$_3$ | OCH$_2$ | | |
| 335 | 2,3,4,6-(CH$_3$)$_4$ | OCH$_2$ | | |
| 336 | 2,3,5,6-(CH$_3$)$_4$ | OCH$_2$ | | |
| 337 | 2,3,4,5,6,-(CH$_3$)$_5$ | OCH$_2$ | | |
| 338 | 2-C$_2$H$_5$ | OCH$_2$ | | |
| 339 | 3-C$_2$H$_5$ | OCH$_2$ | | |
| 340 | 4-C$_2$H$_5$ | OCH$_2$ | | |
| 341 | 2,4-(C$_2$H$_5$)$_2$ | OCH$_2$ | | |
| 342 | 2,6-(C$_2$H$_5$)$_2$ | OCH$_2$ | | |
| 343 | 3,5-(C$_2$H$_5$)$_2$ | OCH$_2$ | | |
| 344 | 2,4,6-(C$_2$H$_5$)$_3$ | OCH$_2$ | | |
| 345 | 2-n-C$_3$H$_7$ | OCH$_2$ | | |
| 346 | 3-n-C$_3$H$_7$ | OCH$_2$ | | |
| 347 | 4-n-C$_3$H$_7$ | OCH$_2$ | | |
| 348 | 2-i-C$_2$H$_7$ | OCH$_2$ | | |
| 349 | 3-i-C$_2$H$_7$ | OCH$_2$ | | |
| 350 | 4-i-C$_3$H$_7$ | OCH$_2$ | | |
| 351 | 2,4-(i-C$_3$H$_7$)$_2$ | OCH$_2$ | | |
| 352 | 2,6-(i-C$_3$H$_7$)$_2$ | OCH$_2$ | | |
| 353 | 2,4,6-(i-C$_3$H$_7$)$_3$ | OCH$_2$ | | |
| 354 | 2,4,6-(i-C$_3$H$_7$)$_3$ | OCH$_2$ | | |
| 355 | 2-s-C$_4$H$_9$ | OCH$_2$ | | |
| 356 | 3-s-C$_4$H$_9$ | OCH$_2$ | | |
| 357 | 4-s-C$_4$H$_9$ | OCH$_2$ | | |
| 358 | 2-t-C$_4$H$_9$ | OCH$_2$ | | |
| 359 | 3-t-C$_4$H$_9$ | OCH$_2$ | | |
| 360 | 4-t-C$_4$H$_9$ | OCH$_2$ | | |

TABLE 1-continued

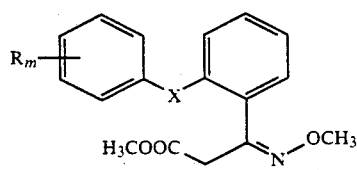

(I)

| No. | $R_m$ | X | mp (°C.) | IR(cm$^{-1}$) |
|---|---|---|---|---|
| 361 | 2,3-(t-C$_4$H$_9$)$_2$ | OCH$_2$ | | |
| 362 | 2,4-(t-C$_4$H$_9$)$_2$ | OCH$_2$ | | |
| 363 | 2,5-(t-C$_4$H$_9$)$_2$ | OCH$_2$ | | |
| 364 | 2,6-(t-C$_4$H$_9$)$_2$ | OCH$_2$ | | |
| 365 | 3,5-(t-C$_4$H$_9$)$_2$ | OCH$_2$ | | |
| 366 | 2,4,6-(t-C$_4$H$_9$)$_3$ | OCH$_2$ | | |
| 367 | 4-n-C$_9$H$_{19}$ | OCH$_2$ | | |
| 368 | 4-n-C$_{12}$H$_{25}$ | OCH$_2$ | | |
| 369 | 3-n-C$_{15}$H$_{31}$ | OCH$_2$ | | |
| 370 | 4-(1,1,3,3,-tetramethylbutyl) | OCH$_2$ | | |
| 371 | 4-(1,1,3,-trimethylbutyl) | OCH$_2$ | | |
| 372 | 2-t-C$_4$H$_9$, 4-CH$_3$ | OCH$_2$ | | |
| 373 | 2-t-C$_4$H$_9$, 5-CH$_3$ | OCH$_2$ | | |
| 374 | 2,6-(t-C$_4$H$_9$)$_2$, 4-CH$_3$ | OCH$_2$ | | |
| 375 | 2-CH$_3$, 4-t-C$_4$H$_9$ | OCH$_2$ | | |
| 376 | 2-CH$_3$, 6-t-C$_4$H$_9$ | OCH$_2$ | | |
| 377 | 2-CH$_3$, 4-i-C$_3$H$_7$ | OCH$_2$ | | |
| 378 | 2-CH$_3$, 5-i-C$_3$H$_7$ | OCH$_2$ | | |
| 379 | 3-CH$_3$, 4-i-C$_3$H$_7$ | OCH$_2$ | | |
| 380 | 2-i-C$_3$H$_7$, 5-CH$_3$ | OCH$_2$ | | |
| 381 | 2,4-(t-C$_4$H$_9$)$_2$, 6-i-C$_3$H$_7$ | OCH$_2$ | | |
| 382 | 2-C$_3$H$_5$ (= allyl) | OCH$_2$ | | |
| 383 | 3-C$_3$H$_5$ | OCH$_2$ | | |
| 384 | 4-C$_3$H$_5$ | OCH$_2$ | | |
| 385 | 2-C$_3$H$_5$, 6-CH$_3$ | OCH$_2$ | | |
| 386 | 2-cyclo-C$_6$H$_{11}$ | OCH$_2$ | | |
| 387 | 3-cyclo-C$_6$H$_{11}$ | OCH$_2$ | | |
| 388 | 4-cyclo-C$_6$H$_{11}$ | OCH$_2$ | | |
| 389 | 2,4-(cyclo-C$_6$H$_{11}$)$_2$, 6-CH$_3$ | OCH$_2$ | | |
| 390 | 2-CH$_3$, 4-cyclo-C$_6$H$_{11}$ | OCH$_2$ | | |
| 391 | 2-CH$_3$, 4-(1,1,3,3-tetramethylbutyl) | OCH$_2$ | | |
| 392 | 2-CH$_2$C$_6$H$_5$ | OCH$_2$ | | |
| 393 | 3-CH$_2$C$_6$H$_5$ | OCH$_2$ | | |
| 394 | 4-CH$_2$C$_6$H$_5$ | OCH$_2$ | | |
| 395 | 2-CH$_2$C$_6$H$_5$, 4-CH$_3$ | OCH$_2$ | | |
| 396 | 2-CH$_3$, 4-CH$_2$C$_6$H$_5$ | OCH$_2$ | | |
| 397 | 2-C$_6$H$_5$ | OCH$_2$ | | |
| 398 | 3-C$_6$H$_5$ | OCH$_2$ | | |
| 399 | 4-C$_6$H$_5$ | OCH$_2$ | | |
| 400 | 4-(2-i-C$_3$H$_7$—C$_6$H$_4$) | OCH$_2$ | | |
| 401 | 4-C$_6$H$_5$, 2,6-(CH$_3$)$_2$ | OCH$_2$ | | |
| 402 | 2-Cl, 4-C$_6$H$_5$ | OCH$_2$ | | |
| 403 | 2-Br, 4-C$_6$H$_5$ | OCH$_2$ | | |
| 404 | 2-C$_6$H$_5$, 4-Cl | OCH$_2$ | | |
| 405 | 2-C$_6$H$_5$, 4-Br | OCH$_2$ | | |
| 406 | 2-CH$_2$C$_6$H$_5$, 4-Cl | OCH$_2$ | | |
| 407 | 2-CH$_2$C$_6$H$_5$, 4-Br | OCH$_2$ | | |
| 408 | 2-Cl, 4-CH$_2$C$_6$H$_5$ | OCH$_2$ | | |
| 409 | 2-Br, 4-CH$_2$C$_6$H$_5$ | OCH$_2$ | | |
| 410 | 2-cyclo-C$_6$H$_{11}$, 4-Cl | OCH$_2$ | | |
| 411 | 2-cyclo-C$_6$H$_{11}$, 4-Br | OCH$_2$ | | |
| 412 | 2-Cl, 4-cyclo-C$_6$H$_{11}$ | OCH$_2$ | | |
| 413 | 2-Br, 4-cyclo-C$_6$H$_{11}$ | OCH$_2$ | | |
| 414 | 2-OCH$_3$ | OCH$_2$ | | |
| 415 | 3-OCH$_3$ | OCH$_2$ | | |
| 416 | 4-OCH$_3$ | OCH$_2$ | | |
| 417 | 2,4-(OCH$_3$)$_2$ | OCH$_2$ | | |
| 418 | 2-OC$_2$H$_5$ | OCH$_2$ | | |
| 419 | 3-OC$_2$H$_5$ | OCH$_2$ | | |
| 420 | 4-OC$_2$H$_5$ | OCH$_2$ | | |
| 421 | 2-OCH$_2$C$_6$H$_5$ | OCH$_2$ | | |
| 422 | 3-OCH$_2$C$_6$H$_5$ | OCH$_2$ | | |
| 423 | 4-OCH$_2$C$_6$H$_5$ | OCH$_2$ | | |
| 424 | 2-O-t-C$_4$H$_9$ | OCH$_2$ | | |
| 425 | 3-O-t-C$_4$H$_9$ | OCH$_2$ | | |
| 426 | 4-O-t-C$_4$H$_9$ | OCH$_2$ | | |
| 427 | 2-OC$_6$H$_5$ | OCH$_2$ | | |
| 428 | 3-OC$_6$H$_5$ | OCH$_2$ | | |
| 429 | 4-OC$_6$H$_5$ | OCH$_2$ | | |
| 430 | 2-CF$_3$ | OCH$_2$ | | |
| 431 | 3-CF$_3$ | OCH$_2$ | | |
| 432 | 4-CF$_3$ | OCH$_2$ | | |

TABLE 1-continued

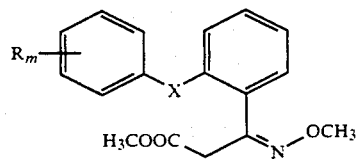
(I)

| No. | $R_m$ | X | mp (°C.) | IR(cm$^{-1}$) |
|---|---|---|---|---|
| 433 | 2-OCF$_3$ | OCH$_2$ | | |
| 434 | 3-OCF$_3$ | OCH$_2$ | | |
| 435 | 4-OCF$_3$ | OCH$_2$ | | |
| 436 | 3-OCH$_2$CHF$_2$ | OCH$_2$ | | |
| 437 | 3-OCF$_2$CHF$_2$ | OCH$_2$ | | |
| 438 | 3-OC$_2$H$_5$ | OCH$_2$ | | |
| 439 | 2-NO$_2$ | OCH$_2$ | | |
| 440 | 3-NO$_2$ | OCH$_2$ | | |
| 441 | 4-NO$_2$ | OCH$_2$ | | |
| 442 | 2-CN | OCH$_2$ | | |
| 443 | 3-CN | OCH$_2$ | | |
| 444 | 4-CN | OCH$_2$ | | |
| 445 | 2-CH$_3$, 3-Cl | OCH$_2$ | | |
| 446 | 2-CH$_3$, 4-Cl | OCH$_2$ | | |
| 447 | 2-CH$_3$, 5-Cl | OCH$_2$ | | |
| 448 | 2-CH$_3$, 6-Cl | OCH$_2$ | | |
| 449 | 2-CH$_3$, 3-F | OCH$_2$ | | |
| 450 | 2-CH$_3$, 4-F | OCH$_2$ | | |
| 451 | 2-CH$_3$, 5-F | OCH$_2$ | | |
| 452 | 2-CH$_3$, 6-F | OCH$_2$ | | |
| 453 | 2-CH$_3$, 3-Br | OCH$_2$ | | |
| 454 | 2-CH$_3$, 4-Br | OCH$_2$ | | |
| 455 | 2-CH$_3$, 5-Br | OCH$_2$ | | |
| 456 | 2-CH$_3$, 6-Br | OCH$_2$ | | |
| 457 | 2-Cl, 3-CH$_3$ | OCH$_2$ | | |
| 458 | 2-Cl, 4-CH$_3$ | OCH$_2$ | | |
| 459 | 2-Cl, 5-CH$_3$ | OCH$_2$ | | |
| 460 | 2-F, 3-CH$_3$ | OCH$_2$ | | |
| 461 | 2-F, 4-CH$_3$ | OCH$_2$ | | |
| 462 | 2-F, 5-CH$_3$ | OCH$_2$ | | |
| 463 | 2-Br, 3-CH$_3$ | OCH$_2$ | | |
| 464 | 2-Br, 4-CH$_3$ | OCH$_2$ | | |
| 465 | 2-Br, 5-CH$_3$ | OCH$_2$ | | |
| 466 | 3-CH$_3$, 4-Cl | OCH$_2$ | | |
| 467 | 3-CH$_3$, 5-Cl | OCH$_2$ | | |
| 468 | 3-CH$_3$, 4-F | OCH$_2$ | | |
| 469 | 3-CH$_3$, 5-F | OCH$_2$ | | |
| 470 | 3-CH$_3$, 4-Br | OCH$_2$ | | |
| 471 | 3-CH$_3$, 5-Br | OCH$_2$ | | |
| 472 | 3-F, 4-CH$_3$ | OCH$_2$ | | |
| 473 | 3-Cl, 4-CH$_3$ | OCH$_2$ | | |
| 474 | 3-Br, 4-CH$_3$ | OCH$_2$ | | |
| 475 | 2-Cl, 4,5-(CH$_3$)$_2$ | OCH$_2$ | | |
| 476 | 2-Br, 4,5-(CH$_3$)$_2$ | OCH$_2$ | | |
| 477 | 2-Cl, 3,5-(CH$_3$)$_2$ | OCH$_2$ | | |
| 478 | 2-Br, 3,5-(CH$_3$)$_2$ | OCH$_2$ | | |
| 479 | 2,6-Cl$_2$, 4-CH$_3$ | OCH$_2$ | | |
| 480 | 2,6-F$_2$, 4-CH$_3$ | OCH$_2$ | | |
| 481 | 2,6-Br$_2$, 4-CH$_3$ | OCH$_2$ | | |
| 482 | 2,4-Cl$_2$, 6-CH$_3$ | OCH$_2$ | | |
| 483 | 2,4-F$_2$, 6-CH$_3$ | OCH$_2$ | | |
| 484 | 2,4-Br$_2$, 6-CH$_3$ | OCH$_2$ | | |
| 485 | 2,6-(CH$_3$)$_2$, 4-F | OCH$_2$ | | |
| 486 | 2,6-(CH$_3$)$_2$, 4-Cl | OCH$_2$ | | |
| 487 | 2,6-(CH$_3$)$_2$, 4-Br | OCH$_2$ | | |
| 488 | 3,5-(CH$_3$)$_2$, 4-F | OCH$_2$ | | |
| 489 | 3,5-(CH$_3$)$_2$, 4-Cl | OCH$_2$ | | |
| 490 | 3,5-(CH$_3$)$_2$, 4-Br | OCH$_2$ | | |
| 491 | 2,3,6-(CH$_3$)$_3$, 4-F | OCH$_2$ | | |
| 492 | 2,3,6-(CH$_3$)$_3$, 4-Cl | OCH$_2$ | | |
| 493 | 2,3,6-(CH$_3$)$_3$, 4-Br | OCH$_2$ | | |
| 494 | 2,4-(CH$_3$)$_2$, 6-F | OCH$_2$ | | |
| 495 | 2,4-(CH$_3$)$_2$, 6-Cl | OCH$_2$ | | |
| 496 | 2,4-(CH$_3$)$_2$, 6-Br | OCH$_2$ | | |
| 497 | 2-i-C$_3$H$_7$, 4-Cl, 5-CH$_3$ | OCH$_2$ | | |
| 498 | 2-CH$_3$, 4-Cl, 5-i-C$_3$H$_7$ | OCH$_2$ | | |
| 499 | 2-Cl, 3-i-C$_3$H$_7$ | OCH$_2$ | | |
| 500 | 2-Cl, 4-i-C$_3$H$_7$ | OCH$_2$ | | |
| 501 | 2-Cl, 4-NO$_2$ | OCH$_2$ | | |
| 502 | 2-NO$_2$, 4-Cl | OCH$_2$ | | |
| 503 | 2-OCH$_3$, 5-NO$_2$ | OCH$_2$ | | |
| 504 | 2,4-Cl$_2$, 5-NO$_2$ | OCH$_2$ | | |

TABLE 1-continued

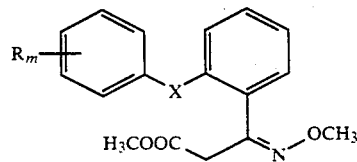
(I)

| No. | $R_m$ | X | mp (°C.) | IR(cm$^{-1}$) |
|---|---|---|---|---|
| 505 | 2,4-Cl$_2$, 6-NO$_2$ | OCH$_2$ | | |
| 506 | 2,6-Cl$_2$, 4-NO$_2$ | OCH$_2$ | | |
| 507 | 2,6-Br$_2$, 4-NO$_2$ | OCH$_2$ | | |
| 508 | 2,6-I$_2$, 4-NO$_2$ | OCH$_2$ | | |
| 509 | H | CH$_2$—CH$_2$ | | |
| 510 | 2-F | CH$_2$—CH$_2$ | | |
| 511 | 3-F | CH$_2$—CH$_2$ | | |
| 512 | 4-F | CH$_2$—CH$_2$ | | |
| 513 | 2,3-F$_2$ | CH$_2$—CH$_2$ | | |
| 514 | 2,4-F$_2$ | CH$_2$—CH$_2$ | | |
| 515 | 2,4,6-F$_3$ | CH$_2$—CH$_2$ | | |
| 516 | 2,3,4,5,6-F$_5$ | CH$_2$—CH$_2$ | | |
| 517 | 2-Cl | CH$_2$—CH$_2$ | | |
| 518 | 3-Cl | CH$_2$—CH$_2$ | | |
| 519 | 4-Cl | CH$_2$—CH$_2$ | | |
| 520 | 2,3-Cl$_2$ | CH$_2$—CH$_2$ | | |
| 521 | 2,4-Cl$_2$ | CH$_2$—CH$_2$ | | |
| 522 | 2,5-Cl$_2$ | CH$_2$—CH$_2$ | | |
| 523 | 2,6-Cl$_2$ | CH$_2$—CH$_2$ | | |
| 524 | 3,4-Cl$_2$ | CH$_2$—CH$_2$ | | |
| 525 | 3,5-Cl$_2$ | CH$_2$—CH$_2$ | | |
| 526 | 2,3,4-Cl$_3$ | CH$_2$—CH$_2$ | | |
| 527 | 2,3,5-Cl$_3$ | CH$_2$—CH$_2$ | | |
| 528 | 2,3,6-Cl$_3$ | CH$_2$—CH$_2$ | | |
| 529 | 2,4,5-Cl$_3$ | CH$_2$—CH$_2$ | | |
| 530 | 2,4,6-Cl$_3$ | CH$_2$—CH$_2$ | | |
| 531 | 3,4,5-Cl$_3$ | CH$_2$—CH$_2$ | | |
| 532 | 2,3,4,6-Cl$_4$ | CH$_2$—CH$_2$ | | |
| 533 | 2,3,5,6-Cl$_4$ | CH$_2$—CH$_2$ | | |
| 534 | 2,3,4,5,6-Cl$_5$ | CH$_2$—CH$_2$ | | |
| 535 | 2-Br | CH$_2$—CH$_2$ | | |
| 536 | 3-Br | CH$_2$—CH$_2$ | | |
| 537 | 4-Br | CH$_2$—CH$_2$ | | |
| 538 | 2,4-Br$_2$ | CH$_2$—CH$_2$ | | |
| 539 | 2,5-Br$_2$ | CH$_2$—CH$_2$ | | |
| 540 | 2,6-Br$_2$ | CH$_2$—CH$_2$ | | |
| 541 | 2,4,6-Br$_3$ | CH$_2$—CH$_2$ | | |
| 542 | 2,3,4,5,6-Br$_5$ | CH$_2$—CH$_2$ | | |
| 543 | 2-I | CH$_2$—CH$_2$ | | |
| 544 | 3-I | CH$_2$—CH$_2$ | | |
| 545 | 4-I | CH$_2$—CH$_2$ | | |
| 546 | 2,4-I$_2$ | CH$_2$—CH$_2$ | | |
| 547 | 2-Cl, 3-F | CH$_2$—CH$_2$ | | |
| 548 | 2-Cl, 4-F | CH$_2$—CH$_2$ | | |
| 549 | 2-Cl, 5-F | CH$_2$—CH$_2$ | | |
| 550 | 2-Cl, 6-F | CH$_2$—CH$_2$ | | |
| 551 | 2-Cl, 3-Br | CH$_2$—CH$_2$ | | |
| 552 | 2-Cl, 4-Br | CH$_2$—CH$_2$ | | |
| 553 | 2-Cl, 5-Br | CH$_2$—CH$_2$ | | |
| 554 | 2-Cl, 6-Br | CH$_2$—CH$_2$ | | |
| 555 | 2-Br, 3-Cl | CH$_2$—CH$_2$ | | |
| 556 | 2-Br, 4-Cl | CH$_2$—CH$_2$ | | |
| 357 | 2-Br, 5-Cl | CH$_2$—CH$_2$ | | |
| 558 | 2-Br, 3-F | CH$_2$—CH$_2$ | | |
| 559 | 2-Br, 4-F | CH$_2$—CH$_2$ | | |
| 560 | 2-Br, 5-F | CH$_2$—CH$_2$ | | |
| 561 | 2-Br, 6-F | CH$_2$—CH$_2$ | | |
| 562 | 2-F, 3-Cl | CH$_2$—CH$_2$ | | |
| 563 | 2-F, 4-Cl | CH$_2$—CH$_2$ | | |
| 564 | 2-F, 5-Cl | CH$_2$—CH$_2$ | | |
| 565 | 3-Cl, 4-F | CH$_2$—CH$_2$ | | |
| 566 | 3-Cl, 5-F | CH$_2$—CH$_2$ | | |
| 567 | 3-Cl, 4-Br | CH$_2$—CH$_2$ | | |
| 568 | 3-Cl, 5-Br | CH$_2$—CH$_2$ | | |
| 569 | 3-F, 4-Cl | CH$_2$—CH$_2$ | | |
| 570 | 3-F, 4-Br | CH$_2$—CH$_2$ | | |
| 571 | 3-Br, 4-Cl | CH$_2$—CH$_2$ | | |
| 572 | 3-Br, 4-F | CH$_2$—CH$_2$ | | |
| 573 | 2,6-Cl$_2$, 4-Br | CH$_2$—CH$_2$ | | |
| 574 | 2-CH$_3$ | CH$_2$—CH$_2$ | | |
| 575 | 3-CH$_3$ | CH$_2$—CH$_2$ | | |
| 576 | 4-CH$_3$ | CH$_2$—CH$_2$ | | |

TABLE 1-continued

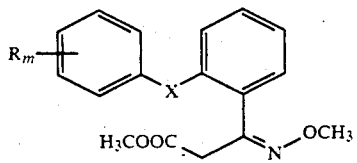

(I)

| No. | $R_m$ | X | mp (°C.) | IR(cm$^{-1}$) |
|---|---|---|---|---|
| 577 | 2,3-(CH$_3$)$_2$ | CH$_2$—CH$_2$ | | |
| 578 | 2,4-(CH$_3$)$_2$ | CH$_2$—CH$_2$ | | |
| 579 | 2,5-(CH$_3$)$_2$ | CH$_2$—CH$_2$ | | |
| 580 | 2,6-(CH$_3$)$_2$ | CH$_2$—CH$_2$ | | |
| 581 | 3,4-(CH$_3$)$_2$ | CH$_2$—CH$_2$ | | |
| 582 | 3,5-(CH$_3$)$_2$ | CH$_2$—CH$_2$ | | |
| 583 | 2,3,4-(CH$_3$)$_3$ | CH$_2$—CH$_2$ | | |
| 584 | 2,3,5-(CH$_3$)$_3$ | CH$_2$—CH$_2$ | | |
| 585 | 2,4,5-(CH$_3$)$_3$ | CH$_2$—CH$_2$ | | |
| 587 | 2,4,6-(CH$_3$)$_3$ | CH$_2$—CH$_2$ | | |
| 588 | 3,4,5-(CH$_3$)$_3$ | CH$_2$—CH$_2$ | | |
| 589 | 2,3,4,6-(CH$_3$)$_4$ | CH$_2$—CH$_2$ | | |
| 590 | 2,3,5,6-(CH$_3$)$_4$ | CH$_2$—CH$_2$ | | |
| 591 | 2,3,4,5,6-(CH$_3$)$_5$ | CH$_2$—CH$_2$ | | |
| 592 | 2-C$_2$H$_5$ | CH$_2$—CH$_2$ | | |
| 593 | 3-C$_2$H$_5$ | CH$_2$—CH$_2$ | | |
| 594 | 4-C$_2$H$_5$ | CH$_2$—CH$_2$ | | |
| 595 | 2,4-(C$_2$H$_5$)$_2$ | CH$_2$—CH$_2$ | | |
| 596 | 2,6-(C$_2$H$_5$)$_2$ | CH$_2$—CH$_2$ | | |
| 597 | 3,5-(C$_2$H$_5$)$_2$ | CH$_2$—CH$_2$ | | |
| 598 | 2,4,6-(C$_2$H$_5$)$_3$ | CH$_2$—CH$_2$ | | |
| 599 | 2-n-C$_3$H$_7$ | CH$_2$—CH$_2$ | | |
| 600 | 3-n-C$_3$H$_7$ | CH$_2$—CH$_2$ | | |
| 601 | 4-n-C$_3$H$_7$ | CH$_2$—CH$_2$ | | |
| 602 | 2-i-C$_3$H$_7$ | CH$_2$—CH$_2$ | | |
| 603 | 3-i-C$_3$H$_7$ | CH$_2$—CH$_2$ | | |
| 604 | 4-i-C$_3$H$_7$ | CH$_2$—CH$_2$ | | |
| 605 | 2,4-(i-C$_3$H$_7$)$_2$ | CH$_2$—CH$_2$ | | |
| 606 | 2,6-(i-C$_3$H$_7$)$_2$ | CH$_2$—CH$_2$ | | |
| 607 | 2,4,6-(i-C$_3$H$_7$)$_3$ | CH$_2$—CH$_2$ | | |
| 608 | 2,4,6-(i-C$_3$H$_7$)$_3$ | CH$_2$—CH$_2$ | | |
| 609 | 2-s-C$_4$H$_9$ | CH$_2$—CH$_2$ | | |
| 610 | 3-s-C$_4$H$_9$ | CH$_2$—CH$_2$ | | |
| 611 | 4-s-C$_4$H$_9$ | CH$_2$—CH$_2$ | | |
| 612 | 2-t-C$_4$H$_9$ | CH$_2$—CH$_2$ | | |
| 613 | 3-t-C$_4$H$_9$ | CH$_2$—CH$_2$ | | |
| 614 | 4-t-C$_4$H$_9$ | CH$_2$—CH$_2$ | | |
| 615 | 2,3-(t-C$_4$H$_9$)$_2$ | CH$_2$—CH$_2$ | | |
| 616 | 2,4-(t-C$_4$H$_9$)$_2$ | CH$_2$—CH$_2$ | | |
| 617 | 2,5-(t-C$_4$H$_9$)$_2$ | CH$_2$—CH$_2$ | | |
| 618 | 2,6-(t-C$_4$H$_9$)$_2$ | CH$_2$—CH$_2$ | | |
| 619 | 3,5-(t-C$_4$H$_9$)$_2$ | CH$_2$—CH$_2$ | | |
| 620 | 2,4,6-(t-C$_4$H$_9$)$_3$ | CH$_2$—CH$_2$ | | |
| 621 | 4-n-C$_9$H$_{19}$ | CH$_2$—CH$_2$ | | |
| 622 | 4-n-C$_{12}$H$_{25}$ | CH$_2$—CH$_2$ | | |
| 623 | 3-n-C$_{15}$H$_{31}$ | CH$_2$—CH$_2$ | | |
| 624 | 4-(1,1,3,3,-tetramethylbutyl) | CH$_2$—CH$_2$ | | |
| 625 | 4-(1,1,3,-trimethylbutyl) | CH$_2$—CH$_2$ | | |
| 626 | 2-t-C$_4$H$_9$, 4-CH$_3$ | CH$_2$—CH$_2$ | | |
| 627 | 2-t-C$_4$H$_9$, 5-CH$_3$ | CH$_2$—CH$_2$ | | |
| 628 | 2,6-(t-C$_4$H$_9$)$_2$, 4-CH$_3$ | CH$_2$CH$_2$ | | |
| 629 | 2-CH$_3$, 4-t-C$_4$H$_9$ | CH$_2$—CH$_2$ | | |
| 630 | 2-CH$_3$, 6-t-C$_4$H$_9$ | CH$_2$—CH$_2$ | | |
| 631 | 2-CH$_3$, 4-i-C$_3$H$_7$ | CH$_2$—CH$_2$ | | |
| 632 | 2-CH$_3$, 5-i-C$_3$H$_7$ | CH$_2$—CH$_2$ | | |
| 633 | 3-CH$_3$, 4-i-C$_3$H$_7$ | CH$_2$—CH$_2$ | | |
| 634 | 2-i-C$_3$H$_7$, 5-CH$_3$ | CH$_2$—CH$_2$ | | |
| 635 | 2,4-(t-C$_4$H$_9$)$_2$, 6-i-C$_3$H$_7$ | CH$_2$—CH$_2$ | | |
| 636 | 2-C$_3$H$_5$ (= Allyl) | CH$_2$—CH$_2$ | | |
| 637 | 3-C$_3$H$_5$ | CH$_2$—CH$_2$ | | |
| 638 | 4-C$_3$H$_5$ | CH$_2$—CH$_2$ | | |
| 639 | 2-C$_3$H$_5$, 6-CH$_3$ | CH$_2$—CH$_2$ | | |
| 640 | 2-cyclo-C$_6$H$_{11}$ | CH$_2$—CH$_2$ | | |
| 641 | 3-cyclo-C$_6$H$_{11}$ | CH$_2$—CH$_2$ | | |
| 642 | 4-cyclo-C$_6$H$_{11}$ | CH$_2$—CH$_2$ | | |
| 643 | 2,4-(cyclo-C$_6$H$_{11}$)$_2$, 6-CH$_3$ | CH$_2$—CH$_2$ | | |
| 644 | 2-CH$_3$, 4-cyclo-C$_6$H$_{11}$ | CH$_2$—CH$_2$ | | |
| 645 | 2-CH$_3$, 4-(1,1,3,3-tetramethylbutyl) | CH$_2$—CH$_2$ | | |
| 646 | 2-CH$_2$C$_6$H$_5$ | CH$_2$—CH$_2$ | | |
| 647 | 3-CH$_2$C$_6$H$_5$ | CH$_2$—CH$_2$ | | |
| 648 | 4-CH$_2$C$_6$H$_5$ | CH$_2$—CH$_2$ | | |
| 649 | 2-CH$_2$C$_6$H$_5$, 4-CH$_3$ | CH$_2$—CH$_2$ | | |

TABLE 1-continued

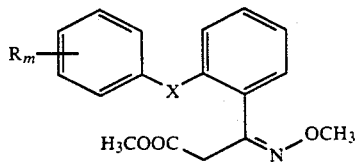

(I)

| No. | $R_m$ | X | mp (°C.) | IR(cm$^{-1}$) |
|---|---|---|---|---|
| 650 | 2-CH$_3$, 4-CH$_2$C$_6$H$_5$ | CH$_2$—CH$_2$ | | |
| 651 | 2-C$_6$H$_5$ | CH$_2$—CH$_2$ | | |
| 652 | 3-C$_6$H$_5$ | CH$_2$—CH$_2$ | | |
| 653 | 4-C$_6$H$_5$ | CH$_2$—CH$_2$ | | |
| 654 | 4-(2-i-C$_3$H$_7$—C$_6$H$_4$) | CH$_2$—CH$_2$ | | |
| 655 | 4-C$_6$H$_5$, 2,6-(CH$_3$)$_2$ | CH$_2$—CH$_2$ | | |
| 656 | 2-Cl, 4-C$_6$H$_5$ | CH$_2$—CH$_2$ | | |
| 657 | 2-Br, 4-C$_6$H$_5$ | CH$_2$—CH$_2$ | | |
| 658 | 2-C$_6$H$_5$, 4-Cl | CH$_2$—CH$_2$ | | |
| 659 | 2-C$_6$H$_5$, 4-Br | CH$_2$—CH$_2$ | | |
| 660 | 2-CH$_2$C$_6$H$_5$, 4-Cl | CH$_2$—CH$_2$ | | |
| 661 | 2-CH$_2$C$_6$H$_5$, 4-Br | CH$_2$—CH$_2$ | | |
| 662 | 2-Cl, 4-CH$_2$C$_6$H$_5$ | CH$_2$—CH$_2$ | | |
| 663 | 2-Br, 4-CH$_2$C$_6$H$_5$ | CH$_2$—CH$_2$ | | |
| 664 | 2-cyclo-C$_6$H$_{11}$, 4-Cl | CH$_2$—CH$_2$ | | |
| 665 | 2-cyclo-C$_6$H$_{11}$, 4-Br | CH$_2$—CH$_2$ | | |
| 666 | 2-Cl, 4-cyclo-C$_6$H$_{11}$ | CH$_2$—CH$_2$ | | |
| 667 | 2-Br, 4-cyclo-C$_6$H$_{11}$ | CH$_2$—CH$_2$ | | |
| 668 | 2-OCH$_3$ | CH$_2$—CH$_2$ | | |
| 669 | 3-OCH$_3$ | CH$_2$—CH$_2$ | | |
| 670 | 4-OCH$_3$ | CH$_2$—CH$_2$ | | |
| 671 | 2,4-(OCH$_3$)$_2$ | CH$_2$—CH$_2$ | | |
| 672 | 2-OC$_2$H$_5$ | CH$_2$—CH$_2$ | | |
| 673 | 3-OC$_2$H$_5$ | CH$_2$—CH$_2$ | | |
| 674 | 4-OC$_2$H$_5$ | CH$_2$—CH$_2$ | | |
| 675 | 2-OCH$_2$C$_6$H$_5$ | CH$_2$—CH$_2$ | | |
| 676 | 3-OCH$_2$C$_6$H$_5$ | CH$_2$—CH$_2$ | | |
| 677 | 4-OCH$_2$C$_6$H$_5$ | CH$_2$—CH$_2$ | | |
| 678 | 2-O-t-C$_4$H$_9$ | CH$_2$—CH$_2$ | | |
| 679 | 3-O-t-C$_4$H$_9$ | CH$_2$—CH$_2$ | | |
| 680 | 4-O-t-C$_4$H$_9$ | CH$_2$—CH$_2$ | | |
| 681 | 2-OC$_6$H$_5$ | CH$_2$—CH$_2$ | | |
| 682 | 3-OC$_6$H$_5$ | CH$_2$—CH$_2$ | | |
| 683 | 4-OC$_6$H$_5$ | CH$_2$—CH$_2$ | | |
| 684 | 2-CF$_3$ | CH$_2$—CH$_2$ | | |
| 685 | 3-CF$_3$ | CH$_2$—CH$_2$ | | |
| 686 | 4-CF$_3$ | CH$_2$—CH$_2$ | | |
| 687 | 2-OCF$_3$ | CH$_2$—CH$_2$ | | |
| 688 | 3-OCF$_3$ | CH$_2$—CH$_2$ | | |
| 689 | 4-OCF$_3$ | CH$_2$—CH$_2$ | | |
| 690 | 3-OCH$_2$CHF$_2$ | CH$_2$—CH$_2$ | | |
| 691 | 3-OCF$_2$CHF$_2$ | CH$_2$—CH$_2$ | | |
| 692 | 3-OC$_2$F$_5$ | CH$_2$—CH$_2$ | | |
| 693 | 2-NO$_2$ | CH$_2$—CH$_2$ | | |
| 694 | 3-NO$_2$ | CH$_2$—CH$_2$ | | |
| 695 | 4-NO$_2$ | CH$_2$—CH$_2$ | | |
| 696 | 2-CN | CH$_2$—CH$_2$ | | |
| 697 | 3-CN | CH$_2$—CH$_2$ | | |
| 698 | 4-CN | CH$_2$—CH$_2$ | | |
| 699 | 2-CH$_3$, 3-Cl | CH$_2$—CH$_2$ | | |
| 700 | 2-CH$_3$, 4-Cl | CH$_2$—CH$_2$ | | |
| 701 | 2-CH$_3$, 5-Cl | CH$_2$—CH$_2$ | | |
| 702 | 2-CH$_3$, 6-Cl | CH$_2$—CH$_2$ | | |
| 703 | 2-CH$_3$, 3-F | CH$_2$—CH$_2$ | | |
| 704 | 2-CH$_3$, 4-F | CH$_2$—CH$_2$ | | |
| 705 | 2-CH$_3$, 5-F | CH$_2$—CH$_2$ | | |
| 706 | 2-CH$_3$, 6-F | CH$_2$—CH$_2$ | | |
| 707 | 2-CH$_3$, 3-Br | CH$_2$—CH$_2$ | | |
| 708 | 2-CH$_3$, 4-Br | CH$_2$—CH$_2$ | | |
| 709 | 2-CH$_3$, 5-Br | CH$_2$—CH$_2$ | | |
| 710 | 2-CH$_3$, 6-Br | CH$_2$—CH$_2$ | | |
| 711 | 2-Cl, 3-CH$_3$ | CH$_2$—CH$_2$ | | |
| 712 | 2-Cl, 4-CH$_3$ | CH$_2$—CH$_2$ | | |
| 713 | 2-Cl, 5-CH$_3$ | CH$_2$—CH$_2$ | | |
| 714 | 2-F, 3-CH$_3$ | CH$_2$—CH$_2$ | | |
| 715 | 2-F, 4-CH$_3$ | CH$_2$—CH$_2$ | | |
| 716 | 2-F, 5-CH$_3$ | CH$_2$—CH$_2$ | | |
| 717 | 2-Br, 3-CH$_3$ | CH$_2$—CH$_2$ | | |
| 718 | 2-Br, 4-CH$_3$ | CH$_2$—CH$_2$ | | |
| 719 | 2-Br, 5-CH$_3$ | CH$_2$—CH$_2$ | | |
| 720 | 3-CH$_3$, 4-Cl | CH$_2$—CH$_2$ | | |
| 721 | 3-CH$_3$, 5-Cl | CH$_2$—CH$_2$ | | |

TABLE 1-continued

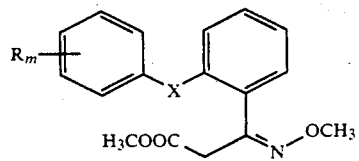
(I)

| No. | $R_m$ | X | mp (°C.) | IR(cm$^{-1}$) |
|---|---|---|---|---|
| 722 | 3-CH$_3$, 4-F | CH$_2$—CH$_2$ | | |
| 723 | 3-CH$_3$, 5-F | CH$_2$—CH$_2$ | | |
| 724 | 3-CH$_3$, 4-Br | CH$_2$—CH$_2$ | | |
| 725 | 3-CH$_3$, 5-Br | CH$_2$—CH$_2$ | | |
| 726 | 3-F, 4-CH$_3$ | CH$_2$—CH$_2$ | | |
| 727 | 3-Cl, 4-CH$_3$ | CH$_2$—CH$_2$ | | |
| 728 | 3-Br, 4-CH$_3$ | CH$_2$—CH$_2$ | | |
| 729 | 2-Cl, 4,5-(CH$_3$)$_2$ | CH$_2$—CH$_2$ | | |
| 730 | 2-Br, 4,5-(CH$_3$)$_2$ | CH$_2$—CH$_2$ | | |
| 731 | 2-Cl, 3,5-(CH$_3$)$_2$ | CH$_2$—CH$_2$ | | |
| 732 | 2-Br, 3,5-(CH$_3$)$_2$ | CH$_2$—CH$_2$ | | |
| 733 | 2,6-Cl$_2$, 4-CH$_3$ | CH$_2$—CH$_2$ | | |
| 734 | 2,6-F$_2$, 4-CH$_3$ | CH$_2$—CH$_2$ | | |
| 735 | 2,6-Br$_2$, 4-CH$_3$ | CH$_2$—CH$_2$ | | |
| 736 | 2,4-Cl$_2$, 6-CH$_3$ | CH$_2$—CH$_2$ | | |
| 737 | 2,4-F$_2$, 6-CH$_3$ | CH$_2$—CH$_2$ | | |
| 738 | 2,4-Br$_2$, 6-CH$_3$ | CH$_2$—CH$_2$ | | |
| 739 | 2,6-(CH$_3$)$_2$, 4-F | CH$_2$—CH$_2$ | | |
| 740 | 2,6-(CH$_3$)$_2$, 4-Cl | CH$_2$—CH$_2$ | | |
| 741 | 2,6-(CH$_3$)$_2$, 4-Br | CH$_2$—CH$_2$ | | |
| 742 | 3,5-(CH$_3$)$_2$, 4-F | CH$_2$—CH$_2$ | | |
| 743 | 3,5-(CH$_3$)$_2$, 4-Cl | CH$_2$—CH$_2$ | | |
| 744 | 3,5-(CH$_3$)$_2$, 4-Br | CH$_2$—CH$_2$ | | |
| 745 | 2,3,6-(CH$_3$)$_3$, 4-F | CH$_2$—CH$_2$ | | |
| 746 | 2,3,6-(CH$_3$)$_3$, 4-Cl | CH$_2$—CH$_2$ | | |
| 747 | 2,3,6-(CH$_3$)$_3$, 4-Br | CH$_2$—CH$_2$ | | |
| 748 | 2,4-(CH$_3$)$_2$, 6-F | CH$_2$—CH$_2$ | | |
| 749 | 2,4-(CH$_3$)$_2$, 6-Cl | CH$_2$—CH$_2$ | | |
| 750 | 2,4-(CH$_3$)$_2$, 6-Br | CH$_2$—CH$_2$ | | |
| 751 | 2-i-C$_3$H$_7$, 4-Cl, 5-CH$_3$ | CH$_2$—CH$_2$ | | |
| 752 | 2-CH$_3$, 4-Cl, 5-i-C$_3$H$_7$ | CH$_2$—CH$_2$ | | |
| 753 | 2-Cl, 3-i-C$_3$H$_7$ | CH$_2$—CH$_2$ | | |
| 754 | 2-Cl, 4-i-C$_3$H$_7$ | CH$_2$—CH$_2$ | | |
| 755 | 2-Cl, 4-NO$_2$ | CH$_2$—CH$_2$ | | |
| 756 | 2-NO$_2$, 4-Cl | CH$_2$—CH$_2$ | | |
| 757 | 2-OCH$_3$, 5-NO$_2$ | CH$_2$—CH$_2$ | | |
| 758 | 2,4-Cl$_2$, 5-NO$_2$ | CH$_2$—CH$_2$ | | |
| 759 | 2,4-Cl$_2$, 6-NO$_2$ | CH$_2$—CH$_2$ | | |
| 760 | 2,6-Cl$_2$, 4-NO$_2$ | CH$_2$—CH$_2$ | | |
| 761 | 2,6-Br$_2$, 4-NO$_2$ | CH$_2$—CH$_2$ | | |
| 762 | 2,6-I$_2$, 4-NO$_2$ | CH$_2$—CH$_2$ | | |
| 763 | H | CH=CH | | |
| 764 | 2-F | CH=CH | | |
| 765 | 3-F | CH=CH | | |
| 766 | 4-F | CH=CH | | |
| 767 | 2,3-F$_2$ | CH=CH | | |
| 768 | 2,4-F$_2$ | CH=CH | | |
| 769 | 2,4,6-F$_3$ | CH=CH | | |
| 770 | 2,3,4,5,6-F$_5$ | CH=CH | | |
| 771 | 2-Cl | CH=CH | | |
| 772 | 3-Cl | CH=CH | | |
| 773 | 4-Cl | CH=CH | | |
| 774 | 2,3-Cl$_2$ | CH=CH | | |
| 775 | 2,4-Cl$_2$ | CH=CH | | |
| 776 | 2,5-Cl$_2$ | CH=CH | | |
| 777 | 2,6-Cl$_2$ | CH=CH | | |
| 778 | 3,4-Cl$_2$ | CH=CH | | |
| 779 | 3,5-Cl$_2$ | CH=CH | | |
| 780 | 2,3,4-Cl$_3$ | CH=CH | | |
| 781 | 2,3,5-Cl$_3$ | CH=CH | | |
| 782 | 2,3,6-Cl$_3$ | CH=CH | | |
| 783 | 2,4,5-Cl$_3$ | CH=CH | | |
| 784 | 2,4,6-Cl$_3$ | CH=CH | | |
| 785 | 3,4,5-Cl$_3$ | CH=CH | | |
| 786 | 2,3,4,6-Cl$_4$ | CH=CH | | |
| 787 | 2,3,5,6-Cl$_4$ | CH=CH | | |
| 788 | 2,3,4,5,6-Cl$_5$ | CH=CH | | |
| 789 | 2-Br | CH=CH | | |
| 790 | 3-Br | CH=CH | | |
| 791 | 4-Br | CH=CH | | |
| 792 | 2,4-Br$_2$ | CH=CH | | |
| 793 | 2,5-Br$_2$ | CH=CH | | |

TABLE 1-continued

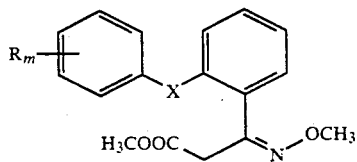

(I)

| No. | $R_m$ | X | mp (°C.) | IR(cm$^{-1}$) |
|---|---|---|---|---|
| 794 | 2,6-Br$_2$ | CH=CH | | |
| 795 | 2,4,6-Br$_3$ | CH=CH | | |
| 796 | 2,3,4,5,6-Br$_5$ | CH=CH | | |
| 797 | 2-I | CH=CH | | |
| 798 | 3-I | CH=CH | | |
| 799 | 4-I | CH=CH | | |
| 800 | 2,4-I$_2$ | CH=CH | | |
| 801 | 2-Cl, 3-F | CH=CH | | |
| 802 | 2-Cl, 4-F | CH=CH | | |
| 803 | 2-Cl, 5-F | CH=CH | | |
| 804 | 2-Cl, 6-F | CH=CH | | |
| 805 | 2-Cl, 3-Br | CH=CH | | |
| 806 | 2-Cl, 4-Br | CH=CH | | |
| 807 | 2-Cl, 5-Br | CH=CH | | |
| 808 | 2-Cl, 6-Br | CH=CH | | |
| 809 | 2-Br, 3-Cl | CH=CH | | |
| 810 | 2-Br, 4-Cl | CH=CH | | |
| 811 | 2-Br, 5-Cl | CH=CH | | |
| 812 | 2-Br, 3-F | CH=CH | | |
| 813 | 2-Br, 4-F | CH=CH | | |
| 814 | 2-Br, 5-F | CH=CH | | |
| 815 | 2-Br, 6-F | CH=CH | | |
| 816 | 2-F, 3-Cl | CH=CH | | |
| 817 | 2-F, 4-Cl | CH=CH | | |
| 818 | 2-F, 5-Cl | CH=CH | | |
| 819 | 3-Cl, 4-F | CH=CH | | |
| 820 | 3-Cl, 5-F | CH=CH | | |
| 821 | 3-Cl, 4-Br | CH=CH | | |
| 822 | 3-Cl, 5-Br | CH=CH | | |
| 823 | 3-F, 4-Cl | CH=CH | | |
| 824 | 3-F, 4-Br | CH=CH | | |
| 825 | 3-Br, 4-Cl | CH=CH | | |
| 826 | 3-Br, 4-F | CH=CH | | |
| 827 | 2,6-Cl$_2$, 4-Br | CH=CH | | |
| 828 | 2-CH$_3$ | CH=CH | | |
| 829 | 3-CH$_3$ | CH=CH | | |
| 830 | 4-CH$_3$ | CH=CH | | |
| 831 | 2,3-(CH$_3$)$_2$ | CH=CH | | |
| 832 | 2,4-(CH$_3$)$_2$ | CH=CH | | |
| 833 | 2,5-(CH$_3$)$_3$ | CH=CH | | |
| 834 | 2,6-(CH$_3$)$_2$ | CH=CH | | |
| 835 | 3,4-(CH$_3$)$_2$ | CH=CH | | |
| 836 | 3,5-(CH$_3$)$_2$ | CH=CH | | |
| 837 | 2,3,4-(CH$_3$)$_3$ | CH=CH | | |
| 838 | 2,3,5-(CH$_3$)$_3$ | CH=CH | | |
| 839 | 2,3,6-(CH$_3$)$_3$ | CH=CH | | |
| 840 | 2,4,5-(CH$_3$)$_3$ | CH=CH | | |
| 841 | 2,4,6-(CH$_3$)$_3$ | CH=CH | | |
| 842 | 3,4,5-(CH$_3$)$_3$ | CH=CH | | |
| 843 | 2,3,4,6-(CH$_3$)$_4$ | CH=CH | | |
| 844 | 2,3,5,6-(CH$_3$)$_4$ | CH=CH | | |
| 845 | 2,3,4,5,6-(CH$_3$)$_5$ | CH=CH | | |
| 846 | 2-C$_2$H$_5$ | CH=CH | | |
| 847 | 3-C$_2$H$_5$ | CH=CH | | |
| 848 | 4-C$_2$H$_5$ | CH=CH | | |
| 849 | 2,4-(C$_2$H$_5$)$_2$ | CH=CH | | |
| 850 | 2,6-(C$_2$H$_5$)$_2$ | CH=CH | | |
| 851 | 3,5-(C$_2$H$_5$)$_2$ | CH=CH | | |
| 852 | 2,4,6-(C$_2$H$_5$)$_3$ | CH=CH | | |
| 853 | 2-n-C$_3$H$_7$ | CH=CH | | |
| 854 | 3-n-C$_3$H$_7$ | CH=CH | | |
| 855 | 4-n-C$_3$H$_7$ | CH=CH | | |
| 856 | 2-i-C$_2$H$_7$ | CH=CH | | |
| 857 | 3-i-C$_2$H$_7$ | CH=CH | | |
| 858 | 4-i-C$_3$H$_7$ | CH=CH | | |
| 859 | 2,4-(i-C$_3$H$_7$)$_2$ | CH=CH | | |
| 860 | 2,6-(i-C$_3$H$_7$)$_2$ | CH=CH | | |
| 861 | 2,4,6-(i-C$_3$H$_7$)$_3$ | CH=CH | | |
| 862 | 2,4,6-(i-C$_3$H$_7$)$_3$ | CH=CH | | |
| 863 | 2-s-C$_4$H$_9$ | CH=CH | | |
| 864 | 3-s-C$_4$H$_9$ | CH=CH | | |
| 865 | 4-s-C$_4$H$_9$ | CH=CH | | |

TABLE 1-continued

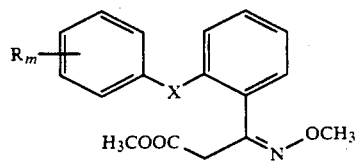
(I)

| No. | $R_m$ | X | mp (°C.) | IR(cm$^{-1}$) |
|---|---|---|---|---|
| 866 | 2-t-C$_4$H$_9$ | CH=CH | | |
| 867 | 3-t-C$_4$H$_9$ | CH=CH | | |
| 868 | 4-t-C$_4$H$_9$ | CH=CH | | |
| 869 | 2,3-(t-C$_4$H$_9$)$_2$ | CH=CH | | |
| 870 | 2,4-(t-C$_4$H$_9$)$_2$ | CH=CH | | |
| 871 | 2,5-(t-C$_4$H$_9$)$_2$ | CH=CH | | |
| 872 | 2,6-(t-C$_4$H$_9$)$_2$ | CH=CH | | |
| 873 | 3,5-(t-C$_4$H$_9$)$_2$ | CH=CH | | |
| 874 | 2,4,6-(t-C$_4$H$_9$)$_3$ | CH=CH | | |
| 875 | 4-n-C$_9$H$_{19}$ | CH=CH | | |
| 876 | 4-n-C$_{12}$H$_{25}$ | CH=CH | | |
| 877 | 3-n-C$_{15}$H$_{31}$ | CH=CH | | |
| 878 | 4-(1,1,3,3,-tetramethylbutyl) | CH=CH | | |
| 879 | 4-(1,1,3,-trimethylbutyl) | CH=CH | | |
| 880 | 2-t-C$_4$H$_9$, 4-CH$_3$ | CH=CH | | |
| 881 | 2-t-C$_4$H$_9$, 5-CH$_3$ | CH=CH | | |
| 882 | 2,6-(t-C$_4$H$_9$)$_2$, 4-CH$_3$ | CH=CH | | |
| 883 | 2-CH$_3$, 4-t-C$_4$H$_9$ | CH=CH | | |
| 884 | 2-CH$_3$, 6-t-C$_4$H$_9$ | CH=CH | | |
| 885 | 2-CH$_3$, 4-i-C$_3$H$_7$ | CH=CH | | |
| 886 | 2-CH$_3$, 5-i-C$_3$H$_7$ | CH=CH | | |
| 887 | 3-CH$_3$, 4-i-C$_3$H$_7$ | CH=CH | | |
| 888 | 2-i-C$_3$H$_7$, 5-CH$_3$ | CH=CH | | |
| 889 | 2,4-(t-C$_4$H$_9$)$_2$, 6-i-C$_3$H$_7$ | CH=CH | | |
| 890 | 2-C$_3$H$_5$ (= allyl) | CH=CH | | |
| 891 | 3-C$_3$H$_5$ | CH=CH | | |
| 892 | 4-C$_3$H$_5$ | CH=CH | | |
| 893 | 2-C$_3$H$_5$, 6-CH$_3$ | CH=CH | | |
| 894 | 2-cyclo-C$_6$H$_{11}$ | CH=CH | | |
| 895 | 3-cyclo-C$_6$H$_{11}$ | CH=CH | | |
| 896 | 4-cyclo-C$_6$H$_{11}$ | CH=CH | | |
| 897 | 2,4-(cyclo-C$_6$H$_{11}$)$_2$, 6-CH$_3$ | CH=CH | | |
| 898 | 2-CH$_3$, 4-cyclo-C$_6$H$_{11}$ | CH=CH | | |
| 899 | 2-CH$_3$, 4-(1,1,3,3-tetramethylbutyl) | CH=CH | | |
| 900 | 2-CH$_2$C$_6$H$_5$ | CH=CH | | |
| 901 | 3-CH$_2$C$_6$H$_5$ | CH=CH | | |
| 902 | 4-CH$_2$C$_6$H$_5$ | CH=CH | | |
| 903 | 2-CH$_2$C$_6$H$_5$, 4-CH$_3$ | CH=CH | | |
| 904 | 2-CH$_3$, 4-CH$_2$C$_6$H$_5$ | CH=CH | | |
| 905 | 2-C$_6$H$_5$ | CH=CH | | |
| 906 | 3-C$_6$H$_5$ | CH=CH | | |
| 907 | 4-C$_6$H$_5$ | CH=CH | | |
| 908 | 4-(2-i-C$_3$H$_7$—C$_6$H$_4$) | CH=CH | | |
| 909 | 4-C$_6$H$_5$, 2,6-(CH$_3$)$_2$ | CH=CH | | |
| 910 | 2-Cl, 4-C$_6$H$_5$ | CH=CH | | |
| 911 | 2-Br, 4-C$_6$H$_5$ | CH=CH | | |
| 912 | 2-C$_6$H$_5$, 4-Cl | CH=CH | | |
| 913 | 2-C$_6$H$_5$, 4-Br | CH=CH | | |
| 914 | 2-CH$_2$C$_6$H$_5$, 4-Cl | CH=CH | | |
| 915 | 2-CH$_2$C$_6$H$_5$, 4-Br | CH=CH | | |
| 916 | 2-Cl, 4-CH$_2$C$_6$H$_5$ | CH=CH | | |
| 917 | 2-Br, 4-CH$_2$C$_6$H$_5$ | CH=CH | | |
| 918 | 2-cyclo-C$_6$H$_{11}$, 4-Cl | CH=CH | | |
| 919 | 2-cyclo-C$_6$H$_{11}$, 4-Br | CH=CH | | |
| 920 | 2-Cl, 4-cyclo-C$_6$H$_{11}$ | CH=CH | | |
| 921 | 2-Br, 4-cyclo-C$_6$H$_{11}$ | CH=CH | | |
| 922 | 2-OCH$_3$ | CH=CH | | |
| 923 | 3-OCH$_3$ | CH=CH | | |
| 924 | 4-OCH$_3$ | CH=CH | | |
| 925 | 2,4-(OCH$_3$)$_2$ | CH=CH | | |
| 926 | 2-OC$_2$H$_5$ | CH=CH | | |
| 927 | 3-OC$_2$H$_5$ | CH=CH | | |
| 928 | 4-OC$_2$H$_5$ | CH=CH | | |
| 929 | 2-OCH$_2$C$_6$H$_5$ | CH=CH | | |
| 930 | 3-OCH$_2$C$_6$H$_5$ | CH=CH | | |
| 931 | 4-OCH$_2$C$_6$H$_5$ | CH=CH | | |
| 932 | 2-O-t-C$_4$H$_9$ | CH=CH | | |
| 933 | 3-O-t-C$_4$H$_9$ | CH=CH | | |
| 934 | 4-O-t-C$_4$H$_9$ | CH=CH | | |
| 935 | 2-OC$_6$H$_5$ | CH=CH | | |
| 936 | 3-OC$_6$H$_5$ | CH=CH | | |
| 937 | 4-OC$_6$H$_5$ | CH=CH | | |

TABLE 1-continued

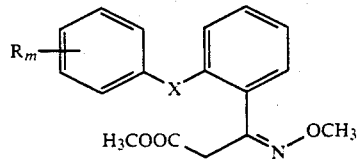

(1)

| No. | $R_m$ | X | mp (°C.) | IR(cm$^{-1}$) |
|---|---|---|---|---|
| 938 | 2-CF$_3$ | CH=CH | | |
| 939 | 3-CF$_3$ | CH=CH | | |
| 940 | 4-CF$_3$ | CH=CH | | |
| 941 | 2-OCF$_3$ | CH=CH | | |
| 942 | 3-OCF$_3$ | CH=CH | | |
| 943 | 4-OCF$_3$ | CH=CH | | |
| 944 | 3-OCH$_2$CHF$_2$ | CH=CH | | |
| 945 | 3-OCF$_2$CHF$_2$ | CH=CH | | |
| 946 | 3-OC$_2$H$_5$ | CH=CH | | |
| 947 | 2-NO$_2$ | CH=CH | | |
| 948 | 3-NO$_2$ | CH=CH | | |
| 949 | 4-NO$_2$ | CH=CH | | |
| 950 | 2-CN | CH=CH | | |
| 951 | 3-CN | CH=CH | | |
| 952 | 4-CN | CH=CH | | |
| 953 | 2-CH$_3$, 3-Cl | CH=CH | | |
| 954 | 2-CH$_3$, 4-Cl | CH=CH | | |
| 955 | 2-CH$_3$, 5-Cl | CH=CH | | |
| 956 | 2-CH$_3$, 6-Cl | CH=CH | | |
| 957 | 2-CH$_3$, 3-F | CH=CH | | |
| 958 | 2-CH$_3$, 4-F | CH=CH | | |
| 959 | 2-CH$_3$, 5-F | CH=CH | | |
| 960 | 2-CH$_3$, 6-F | CH=CH | | |
| 961 | 2-CH$_3$, 3-Br | CH=CH | | |
| 962 | 2-CH$_3$, 4-Br | CH=CH | | |
| 963 | 2-CH$_3$, 5-Br | CH=CH | | |
| 964 | 2-CH$_3$, 6-Br | CH=CH | | |
| 965 | 2-Cl, 3-CH$_3$ | CH=CH | | |
| 966 | 2-Cl, 4-CH$_3$ | CH=CH | | |
| 967 | 2-Cl, 5-CH$_3$ | CH=CH | | |
| 968 | 2-F, 3-CH$_3$ | CH=CH | | |
| 969 | 2-F, 4-CH$_3$ | CH=CH | | |
| 970 | 2-F, 5-CH$_3$ | CH=CH | | |
| 971 | 2-Br, 3-CH$_3$ | CH=CH | | |
| 972 | 2-Br, 4-CH$_3$ | CH=CH | | |
| 973 | 2-Br, 5-CH$_3$ | CH=CH | | |
| 974 | 3-CH$_3$, 4-Cl | CH=CH | | |
| 975 | 3-CH$_3$, 5-Cl | CH=CH | | |
| 976 | 3-CH$_3$, 4-F | CH=CH | | |
| 977 | 3-CH$_3$, 5-F | CH=CH | | |
| 978 | 3-CH$_3$, 4-Br | CH=CH | | |
| 979 | 3-CH$_3$, 5-Br | CH=CH | | |
| 980 | 3-F, 4-CH$_3$ | CH=CH | | |
| 981 | 3-Cl, 4-CH$_3$ | CH=CH | | |
| 982 | 3-Br, 4-CH$_3$ | CH=CH | | |
| 983 | 2-Cl, 4,5-(CH$_3$)$_2$ | CH=CH | | |
| 984 | 2-Br, 4,5-(CH$_3$)$_2$ | CH=CH | | |
| 985 | 2-Cl, 3,5-(CH$_3$)$_2$ | CH=CH | | |
| 986 | 2-Br, 3,5-(CH$_3$)$_2$ | CH=CH | | |
| 987 | 2,6-Cl$_2$, 4-CH$_3$ | CH=CH | | |
| 988 | 2,6-F$_2$, 4-CH$_3$ | CH=CH | | |
| 989 | 2,6-Br$_2$, 4-CH$_3$ | CH=CH | | |
| 990 | 2,4-Cl$_2$, 6-CH$_3$ | CH=CH | | |
| 991 | 2,4-F$_2$, 6-CH$_3$ | CH=CH | | |
| 992 | 2,4-Br$_2$, 6-CH$_3$ | CH=CH | | |
| 993 | 2,6-(CH$_3$)$_2$, 4-F | CH=CH | | |
| 994 | 2,6-(CH$_3$)$_2$, 4-Cl | CH=CH | | |
| 995 | 2,6-(CH$_3$)$_2$, 4-Br | CH=CH | | |
| 996 | 3,5-(CH$_3$)$_2$, 4-F | CH=CH | | |
| 997 | 3,5-(CH$_3$)$_2$, 4-Cl | CH=CH | | |
| 998 | 3,5-(CH$_3$)$_2$, 4-Br | CH=CH | | |
| 999 | 2,3,6-(CH$_3$)$_3$, 4-F | CH=CH | | |
| 1000 | 2,3,6-(CH$_3$)$_3$, 4-Cl | CH=CH | | |
| 1001 | 2,3,6-(CH$_3$)$_3$, 4-Br | CH=CH | | |
| 1002 | 2,4-(CH$_2$)$_2$, 6-F | CH=CH | | |
| 1003 | 2,4-(CH$_3$)$_2$, 6-Cl | CH=CH | | |
| 1004 | 2,4-(CH$_3$)$_2$, 6-Br | CH=CH | | |
| 1005 | 2-i-C$_3$H$_7$, 4-Cl, 5-CH$_3$ | CH=CH | | |
| 1006 | 2-CH$_3$, 4-Cl, 5-i-C$_3$H$_7$ | CH=CH | | |
| 1007 | 2-Cl, 3-i-C$_3$H$_7$ | CH=CH | | |
| 1008 | 2-Cl, 4-i-C$_3$H$_7$ | CH=CH | | |
| 1009 | 2-Cl, 4-NO$_2$ | CH=CH | | |

TABLE 1-continued

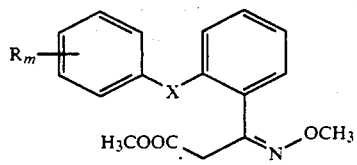

| No. | $R_m$ | X | mp (°C.) | IR(cm$^{-1}$) |
|---|---|---|---|---|
| 1010 | 2-NO$_2$, 4-Cl | CH=CH | | |
| 1011 | 2-OCH$_3$, 5-NO$_2$ | CH=CH | | |
| 1012 | 2,4-Cl$_2$, 5-NO$_2$ | CH=CH | | |
| 1013 | 2,4-Cl$_2$, 6-NO$_2$ | CH=CH | | |
| 1014 | 2,6-Cl$_2$, 4-NO$_2$ | CH=CH | | |
| 1015 | 2,6-Br$_2$, 4-NO$_2$ | CH=CH | | |
| 1016 | 2,6-I$_2$, 4-NO$_2$ | CH=CH | | |
| 1017 | H | SCH$_2$ | | |
| 1018 | 2-F | SCH$_2$ | | |
| 1019 | 3-F | SCH$_2$ | | |
| 1020 | 4-F | SCH$_2$ | | |
| 1021 | 2,3-F$_2$ | SCH$_2$ | | |
| 1022 | 2,4-F$_2$ | SCH$_2$ | | |
| 1023 | 2,4,6-F$_3$ | SCH$_2$ | | |
| 1024 | 2,3,4,5,6-F$_5$ | SCH$_2$ | | |
| 1025 | 2-Cl | SCH$_2$ | | |
| 1026 | 3-Cl | SCH$_2$ | | |
| 1027 | 4-Cl | SCH$_2$ | | |
| 1028 | 2,3-Cl$_2$ | SCH$_2$ | | |
| 1029 | 2,4-Cl$_2$ | SCH$_2$ | | |
| 1030 | 2,5-Cl$_2$ | SCH$_2$ | | |
| 1031 | 2,6-Cl$_2$ | SCH$_2$ | | |
| 1032 | 3,4-Cl$_2$ | SCH$_2$ | | |
| 1033 | 3,5-Cl$_2$ | SCH$_2$ | | |
| 1034 | 2,3,4-Cl$_3$ | SCH$_2$ | | |
| 1035 | 2,3,5-Cl$_3$ | SCH$_2$ | | |
| 1036 | 2,3,6-Cl$_3$ | SCH$_2$ | | |
| 1037 | 2,4,5-Cl$_3$ | SCH$_2$ | | |
| 1038 | 2,4,6-Cl$_3$ | SCH$_2$ | | |
| 1039 | 3,4,5-Cl$_3$ | SCH$_2$ | | |
| 1040 | 2,3,4,6-Cl$_4$ | SCH$_2$ | | |
| 1041 | 2,3,5,6-Cl$_4$ | SCH$_2$ | | |
| 1042 | 2,3,4,5,6-Cl$_5$ | SCH$_2$ | | |
| 1043 | 2-Br | SCH$_2$ | | |
| 1044 | 3-Br | SCH$_2$ | | |
| 1045 | 4-Br | SCH$_2$ | | |
| 1046 | 2,4-Br$_2$ | SCH$_2$ | | |
| 1047 | 2,5-Br$_2$ | SCH$_2$ | | |
| 1048 | 2,6-Br$_2$ | SCH$_2$ | | |
| 1049 | 2,4,6-Br$_3$ | SCH$_2$ | | |
| 1050 | 2,3,4,5,6-Br$_5$ | SCH$_2$ | | |
| 1051 | 2-I | SCH$_2$ | | |
| 1052 | 3-I | SCH$_2$ | | |
| 1053 | 4-I | SCH$_2$ | | |
| 1054 | 2,4-I$_2$ | SCH$_2$ | | |
| 1055 | 2-Cl, 3-F | SCH$_2$ | | |
| 1056 | 2-Cl, 4-F | SCH$_2$ | | |
| 1057 | 2-Cl, 5-F | SCH$_2$ | | |
| 1058 | 2-Cl, 6-F | SCH$_2$ | | |
| 1059 | 2-Cl, 3-Br | SCH$_2$ | | |
| 1060 | 2-Cl, 4-Br | SCH$_2$ | | |
| 1061 | 2-Cl, 5-Br | SCH$_2$ | | |
| 1062 | 2-Cl, 6-Br | SCH$_2$ | | |
| 1063 | 2-Br, 3-Cl | SCH$_2$ | | |
| 1064 | 2-Br, 4-Cl | SCH$_2$ | | |
| 1065 | 2-Br, 5-Cl | SCH$_2$ | | |
| 1066 | 2-Br, 3-F | SCH$_2$ | | |
| 1067 | 2-Br, 4-F | SCH$_2$ | | |
| 1068 | 2-Br, 5-F | SCH$_2$ | | |
| 1069 | 2-Br, 6-F | SCH$_2$ | | |
| 1070 | 2-F, 3-Cl | SCH$_2$ | | |
| 1071 | 2-F, 4-Cl | SCH$_2$ | | |
| 1072 | 2-F, 5-Cl | SCH$_2$ | | |
| 1073 | 3-Cl, 4-F | SCH$_2$ | | |
| 1074 | 3-Cl, 5-F | SCH$_2$ | | |
| 1075 | 3-Cl, 4-Br | SCH$_2$ | | |
| 1076 | 3-Cl, 5-Br | SCH$_2$ | | |
| 1077 | 3-F, 4-Cl | SCH$_2$ | | |
| 1078 | 3-F, 4-Br | SCH$_2$ | | |
| 1079 | 3-Br, 4-Cl | SCH$_2$ | | |
| 1080 | 3-Br, 4-F | SCH$_2$ | | |
| 1081 | 2,6-Cl$_2$, 4-Br | SCH$_2$ | | |

TABLE 1-continued

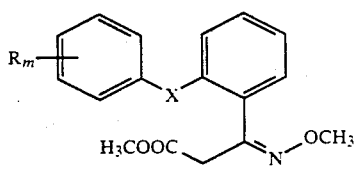

(I)

| No. | $R_m$ | X | mp (°C.) | IR(cm$^{-1}$) |
|---|---|---|---|---|
| 1082 | 2-CH$_3$ | SCH$_2$ | | |
| 1083 | 3-CH$_3$ | SCH$_2$ | | |
| 1084 | 4-CH$_3$ | SCH$_2$ | | |
| 1085 | 2,3-(CH$_3$)$_2$ | SCH$_2$ | | |
| 1086 | 2,4-(CH$_3$)$_2$ | SCH$_2$ | | |
| 1087 | 2,5-(CH$_3$)$_2$ | SCH$_2$ | | |
| 1088 | 2,6-(CH$_3$)$_2$ | SCH$_2$ | | |
| 1089 | 3,4-(CH$_3$)$_2$ | SCH$_2$ | | |
| 1090 | 3,5-(CH$_3$)$_2$ | SCH$_2$ | | |
| 1091 | 2,3,4-(CH$_3$)$_3$ | SCH$_2$ | | |
| 1092 | 2,3,5-(CH$_3$)$_3$ | SCH$_2$ | | |
| 1093 | 2,3,6-(CH$_3$)$_3$ | SCH$_2$ | | |
| 1094 | 2,4,5-(CH$_3$)$_3$ | SCH$_2$ | | |
| 1095 | 2,4,6-(CH$_3$)$_3$ | SCH$_2$ | | |
| 1096 | 3,4,5-(CH$_3$)$_3$ | SCH$_2$ | | |
| 1097 | 2,3,4,6-(CH$_3$)$_4$ | SCH$_2$ | | |
| 1098 | 2,3,5,6-(CH$_3$)$_4$ | SCH$_2$ | | |
| 1099 | 2,3,4,5,6-(CH$_3$)$_5$ | SCH$_2$ | | |
| 1100 | 2-C$_2$H$_5$ | SCH$_2$ | | |
| 1101 | 3-C$_2$H$_5$ | SCH$_2$ | | |
| 1102 | 4-C$_2$H$_5$ | SCH$_2$ | | |
| 1103 | 2,4-(C$_2$H$_5$)$_2$ | SCH$_2$ | | |
| 1104 | 2,6-(C$_2$H$_5$)$_2$ | SCH$_2$ | | |
| 1105 | 3,5-(C$_2$H$_5$)$_2$ | SCH$_2$ | | |
| 1106 | 2,4,6-(C$_2$H$_5$)$_3$ | SCH$_2$ | | |
| 1107 | 2-n-C$_3$H$_7$ | SCH$_2$ | | |
| 1108 | 3-n-C$_3$H$_7$ | SCH$_2$ | | |
| 1109 | 4-n-C$_3$H$_7$ | SCH$_2$ | | |
| 1110 | 2-i-C$_2$H$_7$ | SCH$_2$ | | |
| 1111 | 3-i-C$_2$H$_7$ | SCH$_2$ | | |
| 1112 | 4-i-C$_3$H$_7$ | SCH$_2$ | | |
| 1113 | 2,4-(i-C$_3$H$_7$)$_2$ | SCH$_2$ | | |
| 1114 | 2,6-(i-C$_3$H$_7$)$_2$ | SCH$_2$ | | |
| 1115 | 3,5-(i-C$_3$H$_7$)$_2$ | SCH$_2$ | | |
| 1116 | 2,4,6-(i-C$_3$H$_7$)$_3$ | SCH$_2$ | | |
| 1117 | 2-s-C$_4$H$_9$ | SCH$_2$ | | |
| 1118 | 3-s-C$_4$H$_9$ | SCH$_2$ | | |
| 1119 | 4-s-C$_4$H$_9$ | SCH$_2$ | | |
| 1120 | 2-t-C$_4$H$_9$ | SCH$_2$ | | |
| 1121 | 3-t-C$_4$H$_9$ | SCH$_2$ | | |
| 1122 | 4-t-C$_4$H$_9$ | SCH$_2$ | | |
| 1123 | 2,3-(t-C$_4$H$_9$)$_2$ | SCH$_2$ | | |
| 1124 | 2,4-(t-C$_4$H$_9$)$_2$ | SCH$_2$ | | |
| 1125 | 2,5-(t-C$_4$H$_9$)$_2$ | SCH$_2$ | | |
| 1126 | 2,6-(t-C$_4$H$_9$)$_2$ | SCH$_2$ | | |
| 1127 | 3,5-(t-C$_4$H$_9$)$_2$ | SCH$_2$ | | |
| 1128 | 2,4,6-(t-C$_4$H$_9$)$_3$ | SCH$_2$ | | |
| 1129 | 4-n-C$_9$H$_{19}$ | SCH$_2$ | | |
| 1130 | 4-n-C$_{12}$H$_{25}$ | SCH$_2$ | | |
| 1131 | 3-n-C$_{15}$H$_{31}$ | SCH$_2$ | | |
| 1132 | 4-(1,1,3,3,-tetramethylbutyl) | SCH$_2$ | | |
| 1133 | 4-(1,1,3,-tetramethylbutyl) | SCH$_2$ | | |
| 1134 | 2-t-C$_4$H$_9$, 4-CH$_3$ | SCH$_2$ | | |
| 1135 | 2-t-C$_4$H$_9$, 5-CH$_3$ | SCH$_2$ | | |
| 1136 | 2,6-(t-C$_4$H$_9$)$_2$, 4-CH$_3$ | SCH$_2$ | | |
| 1137 | 2-CH$_3$, 4-t-C$_4$H$_9$ | SCH$_2$ | | |
| 1138 | 2-CH$_3$, 6-t-C$_4$H$_9$ | SCH$_2$ | | |
| 1139 | 2-CH$_3$, 4-i-C$_3$H$_7$ | SCH$_2$ | | |
| 1140 | 2-CH$_3$, 5-i-C$_3$H$_7$ | SCH$_2$ | | |
| 1141 | 3-CH$_3$, 4-i-C$_3$H$_7$ | SCH$_2$ | | |
| 1142 | 2-i-C$_3$H$_7$, 5-CH$_3$ | SCH$_2$ | | |
| 1143 | 2,4-(t-C$_4$H$_9$)$_2$, 6-i-C$_3$H$_7$ | SCH$_2$ | | |
| 1144 | 2-C$_3$H$_5$ (= allyl) | SCH$_2$ | | |
| 1145 | 3-C$_3$H$_5$ | SCH$_2$ | | |
| 1146 | 4-C$_3$H$_5$ | SCH$_2$ | | |
| 1147 | 2-C$_3$H$_5$, 6-CH$_3$ | SCH$_2$ | | |
| 1148 | 2-cyclo-C$_6$H$_{11}$ | SCH$_2$ | | |
| 1149 | 3-cyclo-C$_6$H$_{11}$ | SCH$_2$ | | |
| 1150 | 4-cyclo-C$_6$H$_{11}$ | SCH$_2$ | | |
| 1151 | 2,4-(cyclo-C$_6$H$_{11}$)$_2$, 6-CH$_3$ | SCH$_2$ | | |
| 1152 | 2-CH$_3$, 4-cyclo-C$_6$H$_{11}$ | SCH$_2$ | | |
| 1153 | 2-CH$_3$, 4-(1,1,3,3-tetramethylbutyl) | SCH$_2$ | | |

TABLE 1-continued (I)

Structure: $R_m$—phenyl—X—phenyl—C(=N-OCH$_3$)—CH$_2$—COOCH$_3$

| No. | $R_m$ | X | mp (°C.) | IR(cm$^{-1}$) |
|---|---|---|---|---|
| 1154 | 2-CH$_2$C$_6$H$_5$ | SCH$_2$ | | |
| 1155 | 3-CH$_2$C$_6$H$_5$ | SCH$_2$ | | |
| 1156 | 4-CH$_2$C$_6$H$_5$ | SCH$_2$ | | |
| 1157 | 2-CH$_2$C$_6$H$_5$, 4-CH$_3$ | SCH$_2$ | | |
| 1158 | 2-CH$_3$, 4-CH$_2$C$_6$H$_5$ | SCH$_2$ | | |
| 1159 | 2-C$_6$H$_5$ | SCH$_2$ | | |
| 1160 | 3-C$_6$H$_5$ | SCH$_2$ | | |
| 1161 | 4-C$_6$H$_5$ | SCH$_2$ | | |
| 1162 | 4-(2-i-C$_3$H$_7$—C$_6$H$_4$) | SCH$_2$ | | |
| 1163 | 4-C$_6$H$_5$, 2,6-(CH$_3$)$_2$ | SCH$_2$ | | |
| 1164 | 2-Cl, 4-C$_6$H$_5$ | SCH$_2$ | | |
| 1165 | 2-Br, 4-C$_6$H$_5$ | SCH$_2$ | | |
| 1166 | 2-C$_6$H$_5$, 4-Cl | SCH$_2$ | | |
| 1167 | 2-C$_6$H$_5$, 4-Br | SCH$_2$ | | |
| 1168 | 2-CH$_2$C$_6$H$_5$, 4-Cl | SCH$_2$ | | |
| 1169 | 2-CH$_2$C$_6$H$_5$, 4-Br | SCH$_2$ | | |
| 1170 | 2-Cl, 4-CH$_2$C$_6$H$_5$ | SCH$_2$ | | |
| 1171 | 2-Br, 4-CH$_2$C$_6$H$_5$ | SCH$_2$ | | |
| 1172 | 2-cyclo-C$_6$H$_{11}$, 4-Cl | SCH$_2$ | | |
| 1173 | 2-cyclo-C$_6$H$_{11}$, 4-Br | SCH$_2$ | | |
| 1174 | 2-Cl, 4-cyclo-C$_6$H$_{11}$ | SCH$_2$ | | |
| 1175 | 2-Br, 4-cyclo-C$_6$H$_{11}$ | SCH$_2$ | | |
| 1176 | 2-OCH$_3$ | SCH$_2$ | | |
| 1177 | 3-OCH$_3$ | SCH$_2$ | | |
| 1178 | 4-OCH$_3$ | SCH$_2$ | | |
| 1179 | 2,4-(OCH$_3$)$_2$ | SCH$_2$ | | |
| 1180 | 2-OC$_2$H$_5$ | SCH$_2$ | | |
| 1181 | 3-OC$_2$H$_5$ | SCH$_2$ | | |
| 1182 | 4-OC$_2$H$_5$ | SCH$_2$ | | |
| 1183 | 2-OCH$_2$C$_6$H$_5$ | SCH$_2$ | | |
| 1184 | 3-OCH$_2$C$_6$H$_5$ | SCH$_2$ | | |
| 1185 | 4-OCH$_2$C$_6$H$_5$ | SCH$_2$ | | |
| 1186 | 2-O-t-C$_4$H$_9$ | SCH$_2$ | | |
| 1187 | 3-O-t-C$_4$H$_9$ | SCH$_2$ | | |
| 1188 | 4-O-t-C$_4$H$_9$ | SCH$_2$ | | |
| 1189 | 2-OC$_6$H$_5$ | SCH$_2$ | | |
| 1190 | 3-OC$_6$H$_5$ | SCH$_2$ | | |
| 1191 | 4-OC$_6$H$_5$ | SCH$_2$ | | |
| 1192 | 2-CF$_3$ | SCH$_2$ | | |
| 1193 | 3-CF$_3$ | SCH$_2$ | | |
| 1194 | 4-CF$_3$ | SCH$_2$ | | |
| 1195 | 2-OCF$_3$ | SCH$_2$ | | |
| 1196 | 3-OCF$_3$ | SCH$_2$ | | |
| 1197 | 4-OCF$_3$ | SCH$_2$ | | |
| 1198 | 3-OCH$_2$CHF$_2$ | SCH$_2$ | | |
| 1199 | 3-OCF$_2$CHF$_2$ | SCH$_2$ | | |
| 1200 | 3-OC$_2$F$_5$ | SCH$_2$ | | |
| 1201 | 2-NO$_2$ | SCH$_2$ | | |
| 1202 | 3-NO$_2$ | SCH$_2$ | | |
| 1203 | 4-NO$_2$ | SCH$_2$ | | |
| 1204 | 2-CN | SCH$_2$ | | |
| 1205 | 3-CN | SCH$_2$ | | |
| 1206 | 4-CN | SCH$_2$ | | |
| 1207 | 2-CH$_3$, 3-Cl | SCH$_2$ | | |
| 1208 | 2-CH$_3$, 4-Cl | SCH$_2$ | | |
| 1209 | 2-CH$_3$, 5-Cl | SCH$_2$ | | |
| 1210 | 2-CH$_3$, 6-Cl | SCH$_2$ | | |
| 1211 | 2-CH$_3$, 3-F | SCH$_2$ | | |
| 1212 | 2-CH$_3$, 4-F | SCH$_2$ | | |
| 1213 | 2-CH$_2$, 5-F | SCH$_2$ | | |
| 1214 | 2-CH$_3$, 6-F | SCH$_2$ | | |
| 1215 | 2-CH$_3$, 3-Br | SCH$_2$ | | |
| 1216 | 2-CH$_3$, 4-Br | SCH$_2$ | | |
| 1217 | 2-CH$_3$, 5-Br | SCH$_2$ | | |
| 1218 | 2-CH$_3$, 6-Br | SCH$_2$ | | |
| 1219 | 2-Cl, 3-CH$_3$ | SCH$_2$ | | |
| 1220 | 2-Cl, 4-CH$_3$ | SCH$_2$ | | |
| 1221 | 2-Cl, 5-CH$_3$ | SCH$_2$ | | |
| 1222 | 2-F, 3-CH$_3$ | SCH$_2$ | | |
| 1223 | 2-F, 4-CH$_3$ | SCH$_2$ | | |
| 1224 | 2-F, 5-CH$_3$ | SCH$_2$ | | |
| 1225 | 2-Br, 3-CH$_3$ | SCH$_2$ | | |

TABLE 1-continued

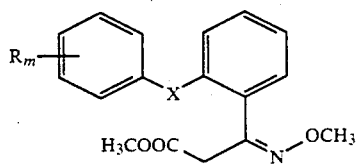

(I)

| No. | $R_m$ | X | mp (°C.) | IR(cm$^{-1}$) |
|---|---|---|---|---|
| 1226 | 2-Br, 4-CH$_3$ | SCH$_2$ | | |
| 1227 | 2-Br, 5-CH$_3$ | SCH$_2$ | | |
| 1228 | 3-CH$_3$, 4-Cl | SCH$_2$ | | |
| 1229 | 3-CH$_3$, 5-Cl | SCH$_2$ | | |
| 1230 | 3-CH$_3$, 4-F | SCH$_2$ | | |
| 1231 | 3-CH$_3$, 5-F | SCH$_2$ | | |
| 1232 | 3-CH$_3$, 4-Br | SCH$_2$ | | |
| 1233 | 3-CH$_3$, 5-Br | SCH$_2$ | | |
| 1234 | 3-F, 4-CH$_3$ | SCH$_2$ | | |
| 1235 | 3-Cl, 4-CH$_3$ | SCH$_2$ | | |
| 1236 | 3-Br, 4-CH$_3$ | SCH$_2$ | | |
| 1237 | 2-Cl, 4,5-(CH$_3$)$_2$ | SCH$_2$ | | |
| 1238 | 2-Br, 4,5-(CH$_3$)$_2$ | SCH$_2$ | | |
| 1239 | 2-Cl, 3,5-(CH$_3$)$_2$ | SCH$_2$ | | |
| 1240 | 2-Br, 3,5-(CH$_3$)$_2$ | SCH$_2$ | | |
| 1241 | 2,6-Cl$_2$, 4-CH$_3$ | SCH$_2$ | | |
| 1242 | 2,6-F$_2$, 4-CH$_3$ | SCH$_2$ | | |
| 1243 | 2,6-Br$_2$, 4-CH$_3$ | SCH$_2$ | | |
| 1244 | 2,4-Cl$_2$, 6-CH$_3$ | SCH$_2$ | | |
| 1245 | 2,4-F$_2$, 6-CH$_3$ | SCH$_2$ | | |
| 1246 | 2,4-Br$_2$, 6-CH$_3$ | SCH$_2$ | | |
| 1247 | 2,6-(CH$_3$)$_2$, 4-F | SCH$_2$ | | |
| 1248 | 2,6-(CH$_3$)$_2$, 4-Cl | SCH$_2$ | | |
| 1249 | 2,6-(CH$_3$)$_2$, 4-Br | SCH$_2$ | | |
| 1250 | 3,5-(CH$_3$)$_2$, 4-F | SCH$_2$ | | |
| 1251 | 3,5-(CH$_3$)$_2$, 4-Cl | SCH$_2$ | | |
| 1252 | 3,5-(CH$_3$)$_2$, 4-Br | SCH$_2$ | | |
| 1253 | 2,3,6-(CH$_3$)$_3$, 4-F | SCH$_2$ | | |
| 1254 | 2,3,6-(CH$_3$)$_3$, 4-Cl | SCH$_2$ | | |
| 1255 | 2,3,6-(CH$_3$)$_3$, 4-Br | SCH$_2$ | | |
| 1256 | 2,4-(CH$_3$)$_2$, 6-F | SCH$_2$ | | |
| 1257 | 2,4-(CH$_3$)$_2$, 6-Cl | SCH$_2$ | | |
| 1258 | 2,4-(CH$_3$)$_2$, 6-Br | SCH$_2$ | | |
| 1259 | 2-i-C$_3$H$_7$, 4-Cl, 5-CH$_3$ | SCH$_2$ | | |
| 1260 | 2-CH$_3$, 4-Cl, 5-i-C$_3$H$_7$ | SCH$_2$ | | |
| 1261 | 2-Cl, 3-i-C$_3$H$_7$ | SCH$_2$ | | |
| 1262 | 2-Cl, 4-i-C$_3$H$_7$ | SCH$_2$ | | |
| 1263 | 2-Cl, 4-NO$_2$ | SCH$_2$ | | |
| 1264 | 2-NO$_2$, 4-Cl | SCH$_2$ | | |
| 1265 | 2-OCH$_3$, 5-NO$_2$ | SCH$_2$ | | |
| 1266 | 2,4-Cl$_2$, 5-NO$_2$ | SCH$_2$ | | |
| 1267 | 2,4-Cl$_2$, 6-NO$_2$ | SCH$_2$ | | |
| 1268 | 2,6-Cl$_2$, 4-NO$_2$ | SCH$_2$ | | |
| 1269 | 2,6-Br$_2$, 4-NO$_2$ | SCH$_2$ | | |
| 1270 | 2,6-I$_2$, 4-NO$_2$ | SCH$_2$ | | |
| 1271 | H | O | | |
| 1272 | 2-F | O | | |
| 1273 | 3-F | O | | |
| 1274 | 4-F | O | | |
| 1275 | 2,3-F$_2$ | O | | |
| 1276 | 2,4-F$_2$ | O | | |
| 1277 | 2,4,6-F$_3$ | O | | |
| 1278 | 2,3,4,5,6-F$_5$ | O | | |
| 1279 | 2-Cl | O | | |
| 1280 | 3-Cl | O | | |
| 1281 | 4-Cl | O | | |
| 1282 | 2,3-Cl$_2$ | O | | |
| 1283 | 2,4-Cl$_2$ | O | | |
| 1284 | 2,5-Cl$_2$ | O | | |
| 1285 | 2,6-Cl$_2$ | O | | |
| 1286 | 3,4-Cl$_2$ | O | | |
| 1287 | 3,5-Cl$_2$ | O | | |
| 1288 | 2,3,4-Cl$_3$ | O | | |
| 1289 | 2,3,5-Cl$_3$ | O | | |
| 1290 | 2,3,6-Cl$_3$ | O | | |
| 1291 | 2,4,5-Cl$_3$ | O | | |
| 1292 | 2,4,6-Cl$_3$ | O | | |
| 1293 | 3,4,5-Cl$_3$ | O | | |
| 1294 | 2,3,4,6-Cl$_4$ | O | | |
| 1295 | 2,3,5,6-Cl$_4$ | O | | |
| 1296 | 2,3,4,5,6-Cl$_5$ | O | | |
| 1297 | 2-Br | O | | |

TABLE 1-continued

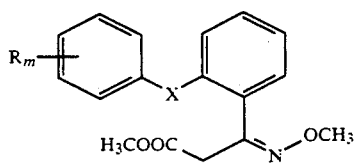

(I)

| No. | $R_m$ | X | mp (°C.) | IR(cm$^{-1}$) |
|---|---|---|---|---|
| 1298 | 3-Br | O | | |
| 1299 | 4-Br | O | | |
| 1300 | 2,4-Br$_2$ | O | | |
| 1301 | 2,5-Br$_2$ | O | | |
| 1302 | 2,6-Br$_2$ | O | | |
| 1303 | 2,4,6-Br$_3$ | O | | |
| 1304 | 2,3,4,5,6-Br$_5$ | O | | |
| 1305 | 2-I | O | | |
| 1306 | 3-I | O | | |
| 1307 | 4-I | O | | |
| 1308 | 2,4-I$_2$ | O | | |
| 1309 | 2-Cl, 3-F | O | | |
| 1310 | 2-Cl, 4-F | O | | |
| 1311 | 2-Cl, 5-F | O | | |
| 1312 | 2-Cl, 6-F | O | | |
| 1313 | 2-Cl, 3-Br | O | | |
| 1314 | 2-Cl, 4-Br | O | | |
| 1315 | 2-Cl, 5-Br | O | | |
| 1316 | 2-Cl, 6-Br | O | | |
| 1317 | 2-Br, 3-Cl | O | | |
| 1318 | 2-Br, 4-Cl | O | | |
| 1319 | 2-Br, 5-Cl | O | | |
| 1320 | 2-Br, 3-F | O | | |
| 1321 | 2-Br, 4-F | O | | |
| 1322 | 2-Br, 5-F | O | | |
| 1323 | 2-Br, 6-F | O | | |
| 1324 | 2-F, 3-Cl | O | | |
| 1325 | 2-F, 4-Cl | O | | |
| 1326 | 2-F, 5-Cl | O | | |
| 1327 | 3-Cl, 4-F | O | | |
| 1328 | 3-Cl, 5-F | O | | |
| 1329 | 3-Cl, 4-Br | O | | |
| 1330 | 3-Cl, 5-Br | O | | |
| 1331 | 3-F, 4-Cl | O | | |
| 1332 | 3-F, 4-Br | O | | |
| 1333 | 3-Br, 4-Cl | O | | |
| 1334 | 3-Br, 4-F | O | | |
| 1335 | 2,6-Cl$_2$, 4-Br | O | | |
| 1336 | 2-CH$_3$ | O | | |
| 1337 | 3-CH$_3$ | O | | |
| 1338 | 4-CH$_3$ | O | | |
| 1339 | 2,3-(CH$_3$)$_2$ | O | | |
| 1340 | 2,4-(CH$_3$)$_2$ | O | | |
| 1341 | 2,5-(CH$_3$)$_2$ | O | | |
| 1342 | 2,6-(CH$_3$)$_2$ | O | | |
| 1343 | 3,4-(CH$_3$)$_2$ | O | | |
| 1344 | 3,5-(CH$_3$)$_2$ | O | | |
| 1345 | 2,3,4-(CH$_3$)$_3$ | O | | |
| 1346 | 2,3,5-(CH$_3$)$_3$ | O | | |
| 1347 | 2,3,6-(CH$_3$)$_3$ | O | | |
| 1348 | 2,4,5-(CH$_3$)$_3$ | O | | |
| 1349 | 2,4,6-(CH$_3$)$_3$ | O | | |
| 1350 | 3,4,5-(CH$_3$)$_3$ | O | | |
| 1351 | 2,3,4,6-(CH$_3$)$_4$ | O | | |
| 1352 | 2,3,5,6-(CH$_3$)$_4$ | O | | |
| 1353 | 2,3,4,5,6-(CH$_3$)$_5$ | O | | |
| 1354 | 2-C$_2$H$_5$ | O | | |
| 1355 | 3-C$_2$H$_5$ | O | | |
| 1356 | 4-C$_2$H$_5$ | O | | |
| 1357 | 2,4-(C$_2$H$_5$)$_2$ | O | | |
| 1358 | 2,6-(C$_2$H$_5$)$_2$ | O | | |
| 1359 | 3,5-(C$_2$H$_5$)$_2$ | O | | |
| 1360 | 2,4,6-(C$_2$H$_5$)$_3$ | O | | |
| 1361 | 2-n-C$_3$H$_7$ | O | | |
| 1362 | 3-n-C$_3$H$_7$ | O | | |
| 1363 | 4-n-C$_3$H$_7$ | O | | |
| 1364 | 2-i-C$_3$H$_7$ | O | | |
| 1365 | 3-i-C$_3$H$_7$ | O | | |
| 1366 | 4-i-C$_3$H$_7$ | O | | |
| 1367 | 2,4-(i-C$_3$H$_7$)$_2$ | O | | |
| 1368 | 2,6-(i-C$_3$H$_7$)$_2$ | O | | |
| 1369 | 3,5-(i-C$_3$H$_7$)$_2$ | O | | |

TABLE 1-continued

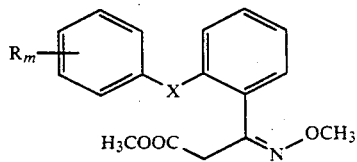

(I)

| No. | $R_m$ | X | mp (°C.) | IR(cm$^{-1}$) |
|---|---|---|---|---|
| 1370 | 2,4,6-(i-C$_3$H$_7$)$_2$ | O | | |
| 1371 | 2-s-C$_4$H$_9$ | O | | |
| 1372 | 3-s-C$_4$H$_9$ | O | | |
| 1373 | 4-s-C$_4$H$_9$ | O | | |
| 1374 | 2-t-C$_4$H$_9$ | O | | |
| 1375 | 3-t-C$_4$H$_9$ | O | | |
| 1376 | 4-t-C$_4$H$_9$ | O | | |
| 1377 | 2,3-(t-C$_4$H$_9$)$_2$ | O | | |
| 1378 | 2,4-(t-C$_4$H$_9$)$_2$ | O | | |
| 1379 | 2,5-(t-C$_4$H$_9$)$_2$ | O | | |
| 1380 | 2,6-(t-C$_4$H$_9$)$_2$ | O | | |
| 1381 | 3,5-(t-C$_4$H$_9$)$_2$ | O | | |
| 1382 | 2,4,6-(t-C$_4$H$_9$)$_3$ | O | | |
| 1383 | 4-n-C$_9$H$_{19}$ | O | | |
| 1384 | 4-n-C$_{12}$H$_{25}$ | O | | |
| 1385 | 3-n-C$_{15}$H$_{31}$ | O | | |
| 1386 | 4-(1,1,3,3,-tetramethylbutyl) | O | | |
| 1387 | 4-(1,1,3,-trimethybutyl) | O | | |
| 1388 | 2-t-C$_4$H$_9$, 4-CH$_3$ | O | | |
| 1389 | 2-t-C$_4$H$_9$, 5-CH$_3$ | O | | |
| 1390 | 2,6-(t-C$_4$H$_9$)$_2$, 4-CH$_3$ | O | | |
| 1391 | 2-CH$_3$, 4-t-C$_4$H$_9$ | O | | |
| 1392 | 2-CH$_3$, 6-t-C$_4$H$_9$ | O | | |
| 1393 | 2-CH$_3$, 4-i-C$_3$H$_7$ | O | | |
| 1394 | 2-CH$_3$, 5-i-C$_3$H$_7$ | O | | |
| 1395 | 3-CH$_3$, 4-i-C$_3$H$_7$ | O | | |
| 1396 | 2-i-C$_3$H$_7$, 5-CH$_3$ | O | | |
| 1397 | 2,4-(t-C$_4$H$_9$)$_2$, 6-i-C$_3$H$_7$ | O | | |
| 1398 | 2-C$_3$H$_5$ (= allyl) | O | | |
| 1399 | 3-C$_3$H$_5$ | O | | |
| 1400 | 4-C$_3$H$_5$ | O | | |
| 1401 | 2-C$_3$H$_5$, 6-CH$_3$ | O | | |
| 1402 | 2-cyclo-C$_6$H$_{11}$ | O | | |
| 1403 | 3-cyclo-C$_6$H$_{11}$ | O | | |
| 1404 | 4-cyclo-C$_6$H$_{11}$ | O | | |
| 1405 | 2,4-(cyclo-C$_6$H$_{11}$)$_2$, 6-CH$_3$ | O | | |
| 1406 | 2-CH$_3$, 4-cyclo-C$_6$H$_{11}$ | O | | |
| 1407 | 2-CH$_3$, 4-(1,1,3,3-tetramethylbutyl) | O | | |
| 1408 | 2-CH$_2$C$_6$H$_5$ | O | | |
| 1409 | 3-CH$_2$C$_6$H$_5$ | O | | |
| 1410 | 4-CH$_2$C$_6$H$_5$ | O | | |
| 1411 | 2-CH$_2$C$_6$H$_5$, 4-CH$_3$ | O | | |
| 1412 | 2-CH$_3$, 4-CH$_2$C$_6$H$_5$ | O | | |
| 1413 | 2-C$_6$H$_5$ | O | | |
| 1414 | 3-C$_6$H$_5$ | O | | |
| 1415 | 4-C$_6$H$_5$ | O | | |
| 1416 | 4-(2-i-C$_3$H$_7$—C$_6$H$_4$) | O | | |
| 1417 | 4-C$_6$H$_5$, 2,6-(CH$_3$)$_2$ | O | | |
| 1418 | 2-Cl, 4-C$_6$H$_5$ | O | | |
| 1419 | 2-Br, 4-C$_6$H$_5$ | O | | |
| 1420 | 2-C$_6$H$_5$, 4-Cl | O | | |
| 1421 | 2-C$_6$H$_5$, 4-Br | O | | |
| 1422 | 2-CH$_2$C$_6$H$_5$, 4-Cl | O | | |
| 1423 | 2-CH$_2$C$_6$H$_5$, 4-Br | O | | |
| 1424 | 2-Cl, 4-CH$_2$C$_6$H$_5$ | O | | |
| 1425 | 2-Br, 4-CH$_2$C$_6$H$_5$ | O | | |
| 1426 | 2-cyclo-C$_6$H$_{11}$, 4-Cl | O | | |
| 1427 | 2-cyclo-C$_6$H$_{11}$, 4-Br | O | | |
| 1428 | 2-Cl, 4-cyclo-C$_6$H$_{11}$ | O | | |
| 1429 | 2-Br, 4-cyclo-C$_6$H$_{11}$ | O | | |
| 1430 | 2-OCH$_3$ | O | | |
| 1431 | 3-OCH$_3$ | O | | |
| 1432 | 4-OCH$_3$ | O | | |
| 1433 | 2,4-(OCH$_3$)$_2$ | O | | |
| 1434 | 2-OC$_2$H$_5$ | O | | |
| 1435 | 3-OC$_2$H$_5$ | O | | |
| 1436 | 4-OC$_2$H$_5$ | O | | |
| 1437 | 2-OCH$_2$C$_6$H$_5$ | O | | |
| 1438 | 3-OCH$_2$C$_6$H$_5$ | O | | |
| 1439 | 4-OCH$_2$C$_6$H$_5$ | O | | |
| 1440 | 2-O-t-C$_4$H$_9$ | O | | |
| 1441 | 3-O-t-C$_4$H$_9$ | O | | |

TABLE 1-continued

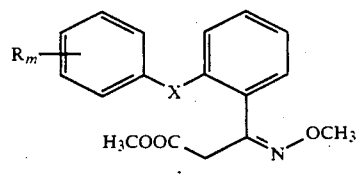

(I)

| No. | $R_m$ | X | mp (°C.) | IR(cm$^{-1}$) |
|---|---|---|---|---|
| 1442 | 4-O-t-C$_4$H$_9$ | O | | |
| 1443 | 2-OC$_6$H$_5$ | O | | |
| 1444 | 3-OC$_6$H$_5$ | O | | |
| 1445 | 4-OC$_6$H$_5$ | O | | |
| 1446 | 2-CF$_3$ | O | | |
| 1447 | 3-CF$_3$ | O | | |
| 1448 | 4-CF$_3$ | O | | |
| 1449 | 2-OCF$_3$ | O | | |
| 1450 | 3-OCF$_3$ | O | | |
| 1451 | 4-OCF$_3$ | O | | |
| 1452 | 3-OCH$_2$CHF$_2$ | O | | |
| 1453 | 3-OCF$_2$CHF$_2$ | O | | |
| 1454 | 3-OC$_2$H$_5$ | O | | |
| 1455 | 2-NO$_2$ | O | | |
| 1456 | 3-NO$_2$ | O | | |
| 1457 | 4-NO$_2$ | O | | |
| 1458 | 2-CN | O | | |
| 1459 | 3-CN | O | | |
| 1460 | 4-CN | O | | |
| 1461 | 2-CH$_3$, 3-Cl | O | | |
| 1462 | 2-CH$_3$, 4-Cl | O | | |
| 1463 | 2-CH$_3$, 5-Cl | O | | |
| 1464 | 2-CH$_3$, 6-Cl | O | | |
| 1465 | 2-CH$_3$, 3-F | O | | |
| 1466 | 2-CH$_3$, 4-F | O | | |
| 1467 | 2-CH$_3$, 5-F | O | | |
| 1468 | 2-CH$_3$, 6-F | O | | |
| 1469 | 2-CH$_3$, 3-Br | O | | |
| 1470 | 2-CH$_3$, 4-Br | O | | |
| 1471 | 2-CH$_3$, 5-Br | O | | |
| 1472 | 2-CH$_3$, 6-Br | O | | |
| 1473 | 2-Cl, 3-CH$_3$ | O | | |
| 1474 | 2-Cl, 4-CH$_3$ | O | | |
| 1475 | 2-Cl, 5-CH$_3$ | O | | |
| 1476 | 2-F, 3-CH$_3$ | O | | |
| 1477 | 2-F, 4-CH$_3$ | O | | |
| 1478 | 2-F, 5-CH$_3$ | O | | |
| 1479 | 2-Br, 3-CH$_3$ | O | | |
| 1480 | 2-Br, 4-CH$_3$ | O | | |
| 1481 | 2-Br, 5-CH$_3$ | O | | |
| 1482 | 3-CH$_3$, 4-Cl | O | | |
| 1483 | 3-CH$_3$, 5-Cl | O | | |
| 1484 | 3-CH$_3$, 4-F | O | | |
| 1485 | 3-CH$_3$, 5-F | O | | |
| 1486 | 3-CH$_3$, 4-Br | O | | |
| 1487 | 3-CH$_3$, 5-Br | O | | |
| 1488 | 3-F, 4-CH$_3$ | O | | |
| 1489 | 3-Cl, 4-CH$_3$ | O | | |
| 1490 | 3-Br, 4-CH$_3$ | O | | |
| 1491 | 2-Cl, 4,5-(CH$_3$)$_2$ | O | | |
| 1492 | 2-Br, 4,5-(CH$_3$)$_2$ | O | | |
| 1493 | 2-Cl, 3,5-(CH$_3$)$_2$ | O | | |
| 1494 | 2-Br, 3,5-(CH$_3$)$_2$ | O | | |
| 1495 | 2,6-Cl$_2$, 4-CH$_3$ | O | | |
| 1496 | 2,6-F$_2$, 4-CH$_3$ | O | | |
| 1497 | 2,6-Br$_2$, 4-CH$_3$ | O | | |
| 1498 | 2,4-Cl$_2$, 6-CH$_3$ | O | | |
| 1499 | 2,4-F$_2$, 6-CH$_3$ | O | | |
| 1500 | 2,4-Br$_2$, 6-CH$_3$ | O | | |
| 1501 | 2,6-(CH$_3$)$_2$, 4-F | O | | |
| 1502 | 2,6-(CH$_3$)$_2$, 4-Cl | O | | |
| 1503 | 2,6-(CH$_3$)$_2$, 4-Br | O | | |
| 1504 | 3,5-(CH$_3$)$_2$, 4-F | O | | |
| 1505 | 3,5-(CH$_3$)$_2$, 4-Cl | O | | |
| 1506 | 3,5-(CH$_3$)$_2$, 4-Br | O | | |
| 1507 | 2,3,6-(CH$_3$)$_3$, 4-F | O | | |
| 1508 | 2,3,6-(CH$_3$)$_3$, 4-Cl | O | | |
| 1509 | 2,3,6-(CH$_3$)$_3$, 4-Br | O | | |
| 1510 | 2,4-(CH$_3$)$_2$, 6-F | O | | |
| 1511 | 2,4-(CH$_3$)$_2$, 6-Cl | O | | |
| 1512 | 2,4-(CH$_3$)$_2$, 6-Br | O | | |
| 1513 | 2-i-C$_3$H$_7$, 4-Cl, 5-CH$_3$ | O | | |

TABLE 1-continued

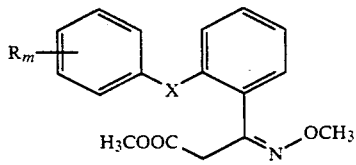

(I)

| No. | $R_m$ | X | mp (°C.) | IR(cm$^{-1}$) |
|---|---|---|---|---|
| 1514 | 2-CH$_3$, 4-Cl, 5-i-C$_3$H$_7$ | O | | |
| 1515 | 2-Cl, 3-i-C$_3$H$_7$ | O | | |
| 1516 | 2-Cl, 4-i-C$_3$H$_7$ | O | | |
| 1517 | 2-Cl, 4-NO$_2$ | O | | |
| 1518 | 2-NO$_2$, 4-Cl | O | | |
| 1519 | 2-OCH$_3$, 5-NO$_2$ | O | | |
| 1520 | 2,4-Cl$_2$, 5-NO$_2$ | O | | |
| 1521 | 2,4-Cl$_2$, 6-NO$_2$ | O | | |
| 1522 | 2,6-Cl$_2$, 4-NO$_2$ | O | | |
| 1523 | 2,6-Br$_2$, 4-NO$_2$ | O | | |
| 1524 | 2,6-I$_2$, 4-NO$_2$ | O | | |
| 1525 | *1) | OCH$_2$ | | |
| 1526 | *2) | OCH$_2$ | | |
| 1527 | *1) | CH$_2$O | | |
| 1528 | *2) | CH$_2$O | | |

*1) 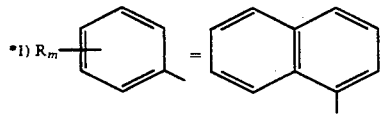

*2) 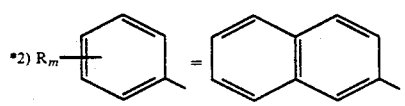

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi. Either the fungi themselves, or the plants, seeds, materials or soil to be protected against fungal attack are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicidal agents generally contain from 0.1 to 95, and preferably from 0.5 to 90, wt. % of active ingredient. The application rates are from 0.02 to 3 kg or more of active ingredient per hectare, depending on the type of effect desired. The novel compounds may also be used for protecting materials (wood), for example against *Paecilomyces variotti*.

When the active ingredients are used for treating seed, amounts of from 0.001 to 50, and preferably from 0.01 to 10, g per kg of seed are usually employed.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 4 is mixed with 10 parts by weight of N-methyl-α-pyrrolidone. A mixture is obtained which is suitable for application in the form of very fine drops.

II. 20 parts by weight of compound no. 11 is dissolved in a mixture consisting of 80 parts by weight of xylene, 10 parts by weight of the adduct of 8 to 10 moles of ethylene oxide and 1 mole of oleic acid N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 66 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 11 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 66 is intimately mixed with 97 parts by weight of particulate kaolin. A dust is obtained containing 3% by weight of the active ingredient.

VII. 30 parts by weight of compound no. 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 11 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 66 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oil dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLE

The active ingredient 2-(2-methylbenzyloxy)-phenylglyoxylic acid methyl ester-O-methyloxime (A) disclosed in EP 253,213 was used for comparison purposes.

ACTION ON *PYRENOPHORA TERES*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results shows that active ingredients 4, 11 and 66, applied as 0.05 wt % spray liquors, have a better fungicidal action (90%) than prior art comparative agent A (60%).

We claim:

1. A compound of the formula I

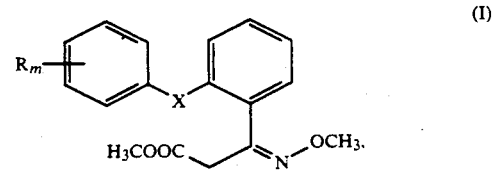

where the radicals R (m = 1 to 5) are identical or different and are each hydrogen, halogen, cyano, nitro, $C_1$-$C_{15}$-alkyl, $C_3$-$C_6$-cycloalkyl, $C_3$-$C_6$-alkenyl, $C_1$-$C_4$-alkoxy, $C_1$-$C_2$-haloalkyl, $C_1$-$C_2$-haloalkoxy, phenyl, $C_1$-$C_4$-alkylphenyl, halophenyl, phenoxy, $C_1$-$C_4$-alkylphenoxy, halophenoxy, benzyl, halobenzyl, benzyloxy, halobenzyloxy, or $C_1$-$C_4$-alkylbenzyloxy or the group

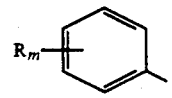

is α-naphthyl or β-naphthyl, and X is methyleneoxy, oxymethylene, ethylene, ethenylene, thiomethylene or oxygen.

2. A process for combating fungi, wherein the fungi, or the materials, plants, seed or soil threatened by fungus attack are treated with a fungicidally effective amount of a compound of the formula I

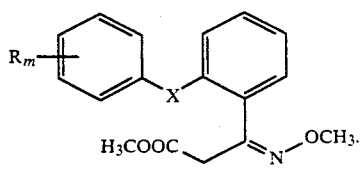

(I)

where the radicals R (m = 1 to 5) are identical or different and are each hydrogen, halogen, cyano, nitro, $C_1$–$C_{15}$-alkyl, $C_3$–$C_6$-cycloalkyl, $C_3$–$C_6$-alkenyl, $C_1$–$C_4$-alkoxy, $C_1$–$C_2$-haloalkyl, $C_1$–$C_2$-haloalkoxy, phenyl, $C_1$–$C_4$-alkylphenyl, halophenyl, phenoxy, $C_1$–$C_4$-alkylphenoxy, halophenoxy, benzyl, halobenzyl, benzyloxy, halobenzyloxy, or $C_1$–$C_4$-alkylbenzyloxy or the group

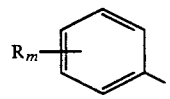

is α-naphthyl or β-naphthyl, and X is methyleneoxy, oxymethylene, ethylene, ethenylene, thiomethylene or oxygen.

3. A fungicide containing an inert carrier and a fungicidally effective amount of a compound of the formula I

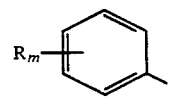

(I)

where the radicals R (m = 1 to 5) are identical or different and are each hydrogen, halogen, cyano, nitro, $C_1$–$C_{15}$-alkyl, $C_3$–$C_6$-cycloalkyl, $C_3$–$C_6$-alkenyl, $C_1$–$C_4$-alkoxy, $C_1$–$C_2$-haloalkyl, $C_1$–$C_2$-haloalkoxy, $C_1$–$C_4$-alkylphenyl, halophenyl, phenoxy, $C_1$–$C_4$-alkylphenoxy, halophenoxy, benzyl, halobenzyl, benzyloxy, halobenzyloxy, or $C_1$–$C_4$-alkylbenzyloxy or the group is α-naphthyl or β-naphthyl, and X is methyleneoxy, oxymethylene, ethylene, ethenylene, thiomethylene or oxygen.

4. A compound of the formula I as set forth in claim 1, where $R_m$ is 2-methyl and X is methyleneoxy.

5. A compound of the formula I as set forth in claim 1, where $R_m$ is 4-fluoro and X is methyleneoxy.

6. A compound of the formula I as set forth in claim 1, where $R_m$ is 4-chloro and X is methyleneoxy.

7. A compound of claim 1, wherein $R_m$ is 2-bromo and X is methyleneoxy.

8. A compound of claim 1, wherein $R_m$ is 3-bromo and X is methyleneoxy.

* * * * *